United States Patent
Vijayasankaran et al.

(10) Patent No.: US 10,676,710 B2
(45) Date of Patent: *Jun. 9, 2020

(54) CELL CULTURE COMPOSITIONS WITH ANTIOXIDANTS AND METHODS FOR POLYPEPTIDE PRODUCTION

(71) Applicant: Genentech, Inc., South San Francisco, CA (US)

(72) Inventors: Natarajan Vijayasankaran, South San Francisco, CA (US); Steven J. Meier, South San Francisco, CA (US); Sharat Varma, South San Francisco, CA (US); Yi Yang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,342

(22) Filed: Jun. 4, 2018

(65) Prior Publication Data

US 2019/0002822 A1 Jan. 3, 2019

Related U.S. Application Data

(63) Continuation of application No. 14/211,416, filed on Mar. 14, 2014, now Pat. No. 10,017,732.

(60) Provisional application No. 61/799,602, filed on Mar. 15, 2013.

(51) Int. Cl.
| | |
|---|---|
| *C12N 5/18* | (2006.01) |
| *A61K 38/00* | (2006.01) |
| *C12N 5/00* | (2006.01) |
| *C07K 16/00* | (2006.01) |

(52) U.S. Cl.
CPC ............ *C12N 5/0018* (2013.01); *C07K 16/00* (2013.01); *C07K 2317/14* (2013.01); *C12N 2500/30* (2013.01); *C12N 2500/33* (2013.01); *C12N 2500/44* (2013.01); *C12N 2500/46* (2013.01)

(58) Field of Classification Search
None
See application file for complete search history.

(56) References Cited

U.S. PATENT DOCUMENTS

| | | |
|---|---|---|
| 3,883,511 A | 5/1975 | Troonen et al. |
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 4/2000 | Carter et al. |
| 6,171,586 B1 | 1/2001 | Lam et al. |
| 6,180,401 B1 | 1/2001 | Chen et al. |
| 6,248,516 B1 | 6/2001 | Winter et al. |
| 6,267,958 B1 | 7/2001 | Andya et al. |
| 6,417,429 B1 | 7/2002 | Hein |
| 6,420,548 B1 | 7/2002 | Vezina et al. |
| 7,078,492 B2 | 7/2006 | Pirofski et al. |
| 7,125,978 B1 | 10/2006 | Vezina et al. |
| 7,153,507 B2 | 12/2006 | Van de Winkel et al. |
| 7,189,826 B2 | 3/2007 | Rodman |
| 7,371,922 B2 | 5/2008 | Wheeler et al. |
| 10,017,732 B2 | 7/2018 | Vijayasankaran |
| 10,131,873 B2 | 11/2018 | Vijayasankaran |
| 2004/0107454 A1 | 6/2004 | Wheeler et al. |
| 2005/0026229 A1 | 2/2005 | Reiter et al. |
| 2005/0100546 A1 | 5/2005 | Jakobovits et al. |
| 2005/0272124 A1 | 12/2005 | Chen et al. |
| 2005/0287149 A1 | 12/2005 | Keler et al. |
| 2006/0059575 A1 | 3/2006 | Kusunoki et al. |

(Continued)

FOREIGN PATENT DOCUMENTS

| | | |
|---|---|---|
| CA | 2 045 208 C | 11/2003 |
| CA | 2 091 636 C | 2/2004 |

(Continued)

OTHER PUBLICATIONS

Anonymous. (2000). *U.S. Pharmacopoeia Inc.* pp. 1926-1927.
Anonymous. (2008). *European Pharmacopoeia* 7*th* Ed., p. 22-24.
Barbas, C.F. et al. (Sep. 1991). "Assembly of Combinatorial Antibody Libraries on Phage Surfaces: The Gene III Site," *Proc. Natl. Acad. Sci. USA* 88:7978-7982.
Barbas, C.F. et al. (May 15, 1992). "Semisynthetic Combinatorial Antibody Libraries: A Chemical Solution to the Diversity Problem," *Proc. Natl. Acad. Sci. USA* 89(10):4457-4461.
Barnes, D. et al. (1980). "Methods for Growth of Cultured Cells in Serum-Free Medium," *Anal. Biochem.* 102:255-270.
Bass, S. et al. (1990). "Hormone Phage: An Enrichment Method for Variant Proteins with Altered Binding Properties," *Proteins* 8(4):309-314.

(Continued)

*Primary Examiner* — Michail A Belyavskyi
(74) *Attorney, Agent, or Firm* — Morrison & Foerster LLP

(57) ABSTRACT

Cell culture media comprising antioxidants are provided herein as are methods of using the media for cell culturing and polypeptide production from cells. Compositions comprising polypeptides, such as therapeutic polypeptides, produced by the methods herein are also provided.

32 Claims, 9 Drawing Sheets

(56) References Cited

U.S. PATENT DOCUMENTS

| | | |
|---|---|---|
| 2006/0147426 A1 | 7/2006 | Schiller et al. |
| 2006/0183887 A1 | 8/2006 | Jakobovits et al. |
| 2006/0258841 A1 | 11/2006 | Michl et al. |
| 2008/0131410 A1 | 6/2008 | Hariri |
| 2008/0274507 A1 | 11/2008 | Gomes et al. |
| 2012/0171161 A1 | 7/2012 | Abramson et al. |
| 2014/0309405 A1 | 10/2014 | Tabuchi et al. |
| 2014/0314779 A1 | 10/2014 | Vijayasankaran |

FOREIGN PATENT DOCUMENTS

| | | |
|---|---|---|
| CN | 102093978 A | 6/2011 |
| DE | 266710 A3 | 4/1989 |
| EP | 0 183 070 A2 | 6/1986 |
| EP | 0 183 070 A3 | 6/1986 |
| EP | 0 183 070 B1 | 6/1986 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 307 247 A2 | 3/1989 |
| EP | 0 307 247 A3 | 3/1989 |
| EP | 0 307 247 B1 | 3/1989 |
| EP | 0 308 936 A2 | 3/1989 |
| EP | 0 402 226 A1 | 12/1990 |
| EP | 0 073 657 B1 | 3/1993 |
| EP | 0 591 605 A2 | 4/1994 |
| JP | H07-507446 A | 8/1995 |
| JP | 2006517399 A | 7/2006 |
| JP | 2006523088 A | 10/2006 |
| JP | 2008540684 A | 11/2008 |
| RU | 2192884 C2 | 11/2002 |
| WO | WO-1987/00195 A1 | 1/1987 |
| WO | WO-1990/03430 A1 | 4/1990 |
| WO | WO-1990/13646 A1 | 11/1990 |
| WO | WO-1991/00360 A1 | 1/1991 |
| WO | WO-1991/10741 A1 | 7/1991 |
| WO | WO-1992/09298 A1 | 6/1992 |
| WO | WO-1992/09690 A2 | 6/1992 |
| WO | WO-1992/09690 A3 | 6/1992 |
| WO | WO-1992/20373 A1 | 11/1992 |
| WO | WO-1993/06213 A1 | 4/1993 |
| WO | WO-1993/08829 A1 | 5/1993 |
| WO | WO-1993/16185 A2 | 8/1993 |
| WO | WO-1993/16185 A3 | 8/1993 |
| WO | WO-1993/18143 A1 | 9/1993 |
| WO | WO-1994/04690 A1 | 3/1994 |
| WO | WO-1994/11026 A2 | 5/1994 |
| WO | WO-1994/11026 A3 | 5/1994 |
| WO | WO-1996/07754 A1 | 3/1996 |
| WO | WO-1996/27011 A1 | 9/1996 |
| WO | WO-1996/33735 A1 | 10/1996 |
| WO | WO-1996/34096 A1 | 10/1996 |
| WO | WO-1998/24893 A2 | 6/1998 |
| WO | WO-1998/24893 A3 | 6/1998 |
| WO | WO-1998/45411 A1 | 10/1998 |
| WO | WO-1998/59035 A2 | 12/1998 |
| WO | WO-1998/59035 A3 | 12/1998 |
| WO | WO-2002/101019 A2 | 12/2002 |
| WO | WO-2002/101019 A3 | 12/2002 |
| WO | WO2004056312 A2 | 7/2004 |
| WO | WO2004058797 A2 | 7/2004 |
| WO | WO-2006/044908 A2 | 4/2006 |
| WO | WO-2006/044908 A3 | 4/2006 |
| WO | WO-2006/089232 A2 | 8/2006 |
| WO | WO-2006/089232 A3 | 8/2006 |
| WO | WO-2006/116034 A1 | 11/2006 |
| WO | WO-2006/116369 A2 | 11/2006 |
| WO | WO-2006/116369 A3 | 11/2006 |
| WO | WO2006125207 A2 | 11/2006 |
| WO | WO-2007/050498 A2 | 5/2007 |
| WO | WO-2007/146123 A2 | 12/2007 |
| WO | WO-2007/146123 A3 | 12/2007 |
| WO | WO-2009/020144 A1 | 2/2009 |
| WO | WO-2011/008770 A2 | 1/2011 |
| WO | WO-2011/019619 A1 | 2/2011 |
| WO | WO-2014/029772 A1 | 9/2014 |

OTHER PUBLICATIONS

Boerner, P. et al. (1991). "Production of Antigen-Specific Human Monoclonal Antibodies From in Vitro-primed Human Splenocytes," *J. Immunol.* 147(1):86-95.

Brennan, M. et al. (Jul. 5, 1985). "Preparation of Bispecific Antibodies by Chemical Recombination of Monoclonal Immunoglobulin G$_1$ Fragments," *Science* 229:81-83.

Brodeur, B.R. et al. (1987). "Mouse-Human Myeloma Partners for the Production of Heterohybridomas," Chapter 4 in *Monoclonal Antibody Production Techniques and Applications*, Marcel Dekker, Inc.: New York, New York, pp. 51-63.

Brüggemann, M. et al. (1993). "Designer Mice: The Production of Human Antibody Repertoires in Transgenic Animals,"*Year in Immuno.* 7:33-40.

Carter, P. et al. (Feb. 1992). "High Level *Escherichia coli* Expression and Production of a Bivalent Humanized Antibody Fragment," *Bio/Technology* 10:163-167.

Carter, P. et al. (May 1992). "Humanization of an Anti-p185$^{HER2}$ Antibody for Human Cancer Therapy," *Proc. Natl. Acad. Sci. USA* 89:4285-4289.

Charlton, K.A. (2003). "Expression and Isolation of Recombinant Antibody Fragments in *E. coli*," Chapter 14 in *Methods in Molecular Biology* Lo, B.K.C. ed., Humana Press: Totowa, NJ, pp. 245-254.

Chothia, C. et al. (1987). "Canonical Structures for the Hypervariable Regions of Immunoglobulins," *J. Mol. Biol.* 196:901-917.

Clackson, T. et al. (Aug. 15, 1991). "Making Antibody Fragments Using Phage Display Libraries," *Nature* 352:624-628.

Daugherty, A.L. et al. (2006). "Formulation and Delivery Issues for Monoclonal Antibody Therapeutics," *Adv. Drug Deliver. Rev.* 58(5-6):686-706.

Duchosal, M.A. et al. (Jan. 16, 1992). "Immunization of hu-PBL-SCID Mice and the Rescue of Human Monoclonal Fab Fragments Through Combinatorial Libraries," *Nature* 355(6357):258-262.

Embleton, M.J. et al. (Aug. 11, 1992). "In-Cell PCR From mRNA: Amplifying and Linking the Rearranged Immunoglobulin Heavy and Light Chain V-Genes Within Single Cells," *Nucl. Acids Res.* 20(15):3831-3837.

Eremeeva, M.E. et al. May 1, 1998). "Effects of the Antioxidant α-lipoic Acid on Human Umbilical Vein Endothelial Cells Infected with *Richkettsii rickettsia*," *Infection and Immunity* 66(5):2290-2299.

Even, M.S. et al. (Mar. 2006). "Serum-Free Hybridoma Culture: Ethical Scientific and Safety Considerations," *Trends in Biotechnology* 24(3):105-108.

Fellouse, F.A. et al. (Aug. 24, 2004). "Synthetic Antibodies From a Four-Amino-Acid Code: A Dominant Role for Tyrosine in Antigen Recognition," *Proc. Natl. Acad. Sci. USA* 101(34):12467-12472.

Fishwild, D.M. et al. (Jul. 1996). "High-avidity Human IgGκ Monoclonal Antibodies From a Novel Strain of Minilocus Transgenic Mice," *Nature Biotechnol.* 14:845-851.

Fleer, R. et al. (Oct. 1991). "Stable Multicopy Vectors for High-Level Secretion of Recombinant Human Serum Albumin by *Kluyveromyces* Yeasts," *Bio/Technology* 9:968-975.

Franek (2005). *Trends in Monoclonal Antibody Research* pp. 111-122.

Gerngross, T.U. (Nov. 2004). "Advances in the Production of Human Therapeutic Proteins in Yeasts and Filamentous Fungi," *Nat. Biotech.* 22(11):1409-1414.

Goding, J.W. (1983). "Production of Monoclonal Antibodies," Chapter 3 in *Monoclonal Antibodies: Principles and Practice*, Academic Press., pp. 56-103, Table of Contents pp. vii-ix.

Graham, F.L. et al. (1977). "Characteristics of a Human Cell Line Transformed by DNA From Human Adenovirus Type 5," *J. Gen. Virol.* 36:59-72.

Gram, H. et al. (Apr. 15, 1992). "*In Vitro* Selection and Affinity Maturations of Antibodies From a Naive Combinatorial Immunoglobulin Library," *Proc. Natl. Acad. Sci. USA* 89:3576-3580.

(56) References Cited

OTHER PUBLICATIONS

Griffiths, A.D. et al. (1993). "Human Anti-Self Antibodies with High Specificity From Phage Display Libraries," *EMBO J.* 12(2):725-734.
Gruber, M. et al. (1994). "Efficient Tumor Cell Lysis Mediated by a Bispecific Single Chain Antibody Expressed in *Escherichia coli*," *J. Immunol.* 152:5368-5374.
Guss, B. et al. (1986). Structure of the IgG-Binding Regions of Streptococcal Protein G, *EMBO J.* 5(7):1567-1575.
Ham, R.G. et al. (1979). "Media and Growth Requirement," Chapter 5 *In Methods in Enzymology*, Academic Press, Inc. 58:44-93.
Hammerling, G.J. et al. Eds. (1981). "Monoclonal Antibodies and T-Cell Hybridomas," Chapter 12 *In Research Monographs in Immunology* Elsevier: New York, NY, 3:563-587.
Hawkins, R.E. et al. (1992). "Selection of Phage Antibodies by Binding Affinity: Mimicking Affinity Maturation," *J. Mol. Biol.* 226:889-896.
Hogrefe, H.H. et al. (Jun. 15, 1993). "A Bacteriophage Lambda Vector for the Cloning and Expression of Immunoglobulin Fab Fragments on the Surface of Filamentous Phage," *Gene* 128(1):119-126.
Holliger, P. et al. (Jul. 1993). "'Diabodies': Small Bivalent and Bispecific Antibody Fragments," *Proc. Natl. Acad. Sci. USA* 90:6444-6448.
Hongo, J-A.S. et al. (1995). "Development and Characterization of Murine Monoclonal Antibodies to the Latency-Associated Peptide of Transforming Growth Factor $\beta_1$," *Hybridoma* 14(3):253-260.
Hoogenboom, H.R. et al. (1991). "Multi-Subunit Proteins on the Surface of Filamentous Phage: Methodologies for Displaying Antibody (Fab) Heavy and Light Chains," *Nucl. Acids Res.* 19(15):4133-4137.
Hoogenboom, H.R. et al. (1992). "By-Passing Immunisation: Human Antibodies From Synthetic Repertoires of Germline $V_H$ Gene Segments Rearranged *in Vitro*," *J. Mol. Biol.* 227:381-388.
Hoogenboom. (2001). *Methods in Molecular Biology* O'Brien et al., Eds., Humana Press: Totowa, N.J. 178:1-37.
Hudson, P.J. et al. (Jan. 2003). "Engineered Antibodies," *Nat. Med.* 9(1):129-134.
International Search Report dated Jul. 24, 2014, for PCT Application No. PCT/US2014/029772, filed on Mar. 14, 2014, 5 pages.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555.
Jakobovits, A. et al. (Mar. 18, 1993). "Germ-line Transmission and Expression of a Human-Derived Yeast Artificial Chromosome," *Nature* 362:255-258.
Jones, E.W. (Jan. 1977). "Proteinase Mutants of *Saccharomyces cerevisiae*," *Genetics* 85:23-33.
Jones, P.T. et al. (May 29, 1986). "Replacing the Complementarity-determining Regions in a Human Antibody With Those From a Mouse," *Nature* 321:522-525.
Jones, S.T. et al. (1991). "Rapid PCR-Cloning of Full-Length Mouse Immunoglobulin Variable Regions", *Biotechnol.* 9:88-89.
Kelley, B. (Sep./Oct. 2009). "Industrialization of mAb Production Technology," *mAbs* 1(5):443-452.
Kohler, G. et al. (Aug. 7, 1975). "Continuous Cultures of Fused Cells Secreting Antibody of Predefined Specificity," *Nature* 256:495-497.
Kostelny, S.A. et al. (Mar. 1, 1992). "Formation of a Bispecific Antibody by the Use of Leucine Zippers," *J. Immunol.* 148(5):1547-1553.
Kozbor, D. (Dec. 1984). "A Human Hybrid Myeloma for Production of Human Monoclonal Antibodies," *J. Immunol.* 133(6):3001-3005.
Lee, C.V. et al. (2004). "Bivalent Antibody Phage Display Mimics Natural Immunoglobulin," *J. Immunol. Methods* 284(1-2):119-132.
Lee, C.V. et al. (2004). "High-Affinity Human Antibodies From Phage-displayed Synthetic Fab Libraries with a Single Framework Scaffold," *J. Mol. Biol.* 340(5):1073-1093.

Leung, D.W. et al. (1989). "A Method for Random Mutagenesis of a Defined DNA Segment Using a Modified Polymerase Chain Reaction", *Technique* 1:11-15.
Li, H. et al. (Feb. 2006, e-pub. Jan. 22, 2006). "Optimization of Humanized IgGs in Glycoengineered *Pichia Pastoris*," *Nat. Biotech.* 24(2):210-215.
Li, F. et al. (Sep./Oct. 2010). "Cell Culture Processes for Monoclonal Antibody Production ," *mAbs* 2(5):466-479.
Lindmark, R. et al. (1983). "Binding of Immunoglobulins to Protein A and Immunoglobulin Levels in Mammalian Sera," *J. Immunol. Meth.* 62:1-13.
Lonberg, N. et al. (Apr. 28, 1994). "Antigen-Specific Human Antibodies from Mice Comprising Four Distinct Genetic Modifications," *Nature* 368:856-859.
Lonberg, N. et al. (1995). "Human Antibodies From Transgenic Mice," *Intern. Rev. Immunol.* 13:65-93.
Marks, J.D. et al.(1991). "By-Passing Immunization: Human Antibodies from V-gene Libraries Displayed on Phage," *J. Mol. Biol.* 222:581-597.
Marks, J.D. et al. (Jul. 1992). "By-Passing Immunization: Building High Affinity Human Antibodies by Chain Shuffling," *Bio/Technology* 10:779-783.
Mather, J.P. (1980). "Establishment and Characterization of Two Distinct Mouse Testicular Epithelial Cell Lines," *Biol. Reprod.* 23:243-252.
Mather, J.P. et al. (1982). "Culture of Testicular Cells in Hormone-Supplemented Serum-Free Medium," *Annals NY Acad. Sci.* 383:44-68.
Matsuda, F. et al. (Jan. 1993). "Structure and Physical Map of 64 Variable Segments in the 3 '0.8-Megabase Region of the Human Immunoglobulin Heavy-Chain Locus," *Nature Genet.* 3(1):88-94.
Mehta, T. R. et al. (Jun. 2001). "Taurine is a Weak Scavenger of Peroxynitrite and Does Not Attenuate Sodium Nitroprusside Toxicity to Cells in Culture," *Amino Acids* 20(4):419-433.
Milstein, C. et al. (Oct. 6, 1983). "Hybrid Hybridomas and Their Use in Immunohistochemistry," *Nature* 305:537-540.
Morimoto, K. et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117.
Morrison, S.L. et al. (Nov. 1984). "Chimeric Human Antibody Molecules: Mouse Antigen- Binding Domains with Human Constant Region Domains," *Proc. Natl. Acad. Sci.* 81:6851-6855.
Morrison, S.L. (Apr. 28, 1994). "Success in Specification," *Nature* 368:812-813.
Mrsny, R.J. et al. (Jan. 21, 1985). "Inhibition of Hamster Sperm $Na^+$, $K^+$-ATPase Activity by Taurine and Hypotaurine," *Life Sciences* 26(3):271-275.
Munson, P.J. et al. (1980). "LIGAND: A Versatile Computerized Approach for Characterization of Ligand-Binding Systems," *Analy. Biochem.* 107:220-239.
Neuberger, M. (Jul. 1996). "Generating High-Avidity Human Mabs in Mice," *Nature Biotechnol.* 14:826.
Ni (2006). *Xiandai Mianyixue* 26(4):265-268.
Orlandi, R. et al. (May 1989). "Cloning Immunoglobulin Variable Domains for Expression by the Polymerase Chain Reaction," *Proc. Natl. Acad. Sci. USA* 86:3833-3837.
Orum, H. et al. (Sep. 24, 1993). "Efficient Method for Constructing Comprehensive Murine Fab Antibody Libraries Displayed on Phage," *Nucleic Acids Res.* 21(19):4491-4498.
Patkar, A. et al. (Feb. 28, 2002). "Flow Cytometry as a Useful Tool for Process Development: Rapid Evaluation of Expression Systems," *J. Biotechnology* 93(3):217-229.
Petters et al. "Addition of Taurine or Hypotaurine to Culture Medium Improves Development of One- and Two-Cell Pig Embryos in Vitro," *Theriogenology* 35(1):253, (Jan. 1991).
Plückthun, A. (1992). "Mono- and Bivalent Antibody Fragments Produced in *Escherichia coli*: Engineering, Folding and Antigen Binding," *Immunol Revs.* 130:151-188.
Presta, L.G. et al. (Sep. 1, 1993). "Humanization of an Antibody Directed Against IgE," *J. Immunol.* 151(5):2623-2632.

(56) References Cited

OTHER PUBLICATIONS

Reyes, G.R. et al. (Jun. 17, 1982). "Expression of Human ß-interferon cDNA Under the Control of a Thymidine Kinase Promoter from Herpes Simplex Virus," *Nature* 297:598-601.
Riechmann, L. et al. (Mar. 24, 1988). "Reshaping Human Antibodies for Therapy," *Nature* 332:323-327.
Sastry, L. et al. (Aug. 1989). "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86(15):5728-5732.
Shalaby, M.R. et al. (Jan. 1, 1992)."Development of Humanized Bispecific Antibodies Reactive with Cytotoxic Lymphocytes and Tumor Cells Overexpressing the *HER2* Protooncogene," *J. Exp. Med.* 175:217-225.
Sidhu, S.S. et al. (2004). "Phage-Displayed Antibody Libraries of Synthetic Heavy Chain Complementarity Determining Regions," *J. Mol. Biol.* 338(2):299-310.
Sims, M.J. et al. (Aug. 15, 1993). "A Humanized CD18 Antibody Can Block Function Without Cell Destruction," *J. Immunol.* 151(4):2296-2308.
Singer, M. et al. (1998). "Genes and Genomes," Moscow, Mir 1:63-64, (English Abstract).
Skerra, A. (1993). "Bacterial Expression of Immunoglobulin Fragments," *Curr. Opinion in Immunol.* 5:256-262.
Stinchcomb, D.T. et al. (Nov. 1, 1979). "Isolation and Characterisation of a Yeast Chromosomal Replicator," *Nature* 282:39-43.
Suresh, M.R. et al. (1986). "Bispecific Monoclonal Antibodies from Hybrid Hybridomas," *Methods in Enzymology* 121:210-228.
Takeuchi, K. et al. (Apr. 5, 2000). "A Hyperosmotic Stress-Induced mRNA of Carp Cell Encodes $Na^+$-and $Cl^-$-Dependent High Affinity Taurine Transporter," *Biochim. Biophys. Acta* 1464(2):219-230.
Tomlinson, I.M. et al. (Oct. 5, 1992). "The Repertoire of Human Germline $V_H$ Sequences Reveals About Fifty Groups of $V_H$ Segments with Different Hypervariable Loops," *J. Mol. Biol.* 227(3):776-798.
Traunecker, A. et al. (1991). "Bispecific Single Chain Molecules (Janusins) Target Cytotoxic Lymphocytes on HIV Infected Cells," *EMBO J.* 10(12):3655-3659.
Tutt, A. et al. (Jul. 1, 1991). "Trispecific F(ab')3 Derivatives That Use Cooperative Signaling Via The TCR/CD3 Complex and CD2 to Activate and Redirect Resting Cytotoxic T Cells" *J. Immunol.* 147:60-69.
Urlaub, G. et al. (Jul. 1980). "Isolation of Chinese Hamster Cell Mutants Deficient in Dihydrofolate Reductase Activity," *Proc. Natl. Acad. Sci. USA* 77(7):4216-4220.
Van Den Berg, J.A. (Feb. 1990). "*Kluyveromyces* As a Host for Heterologous Gene Expression: Expression and Secretion of Prochymosin," *Bio/Technology* 8:135-139.
Verhoeyen, M. et al. (Mar. 25, 1988). "Reshaping Human Antibodies: Grafting an Antilysozyme Activity," *Science* 239:1534-1536.
Vijayasankaran, N. et al. (2005). "Synthesis of poly[(R)-3-hydroxybutyric acid) in the cytoplasm of *Pichia pastoris* under oxygen limitation", *Biomacromolecules*, 6:604-611.
Vijayasankaran, N. et al. (Sep.-Oct. 2013, e-pub. Jun. 27, 2013). "Effect of Cell Culture Medium Components on Color of Formulated Monoclonal Antibody Drug Substance,"*Biotechol. Prag.* 29(5):1270-1277.
Vollmers, H.P. et al. (2005). "The "early birds": Natural IgM Antibodies and Immune Surveillance," *Histology and Histopathology* 20(3):927-937.
Vollmers, H.P. et al. (Apr. 2005). "Death by Stress: Natural IgM-Induced Apoptosis," *Methods and Findings in Experimental and Clinical Pharmacology* 27(3)185-191.
Ward, E.S. et al. (Oct. 12, 1989). "Binding Activities of a Repertoire of Single Immunoglobulin Variable Domains Secreted from *Escherichia coli*," *Nature* 341:544-546.
Wang, X. et al. (Aug. 31, 2010). "New Approved Drugs in the World 2," Beijing: Chemical Industry Press, p. 252, with English Translation, 4 pages.
Waterhouse, P. et al. (1993). "Combinatorial Infection and *in vivo* Recombination: A Strategy for Making Large Phage Antibody Repertoires," *Nucl. Acids Res.* 21(9):2265-2266.
Williams, S.C. et al. (Jul. 1993). "Cloning and Sequencing of Human Immunoglobulin V Lambda Gene Segments," *Eur. J. Immunol.* 23(7):1456-1461.
Winter, G. et al. (1994). "Making Antibodies by Phage Display Technology," *Ann. Rev. Immunol.* 12:433-455.
Written Opinion dated Jul. 24, 2014, for PCT Application No. PCT/US2014/029772, filed on Mar. 14, 2014, 6 pages.
Yanagita et al. "Taurine Reduces the Secretion of Apolipoprotein B100 and Lipids in HepG2 Cells," *Lipids Health Dis.* 7(38):1-6, (Oct. 17, 2008).
Yaniv, M. (May 6, 1982). "Enhancing Elements for Activation of Eukaryotic Promoters," *Nature* 297:17-18.
Yazaki et al. (2003). Expression of Recombinant Antibodies in Mammalian Cell Lines, Chapter 15 *Methods in Molecular Biology* B.K.C. LO, ed. Human Press: Totowa, N.J. 248:255-268.

CELL CULTURE COMPOSITIONS WITH ANTIOXIDANTS AND METHODS FOR POLYPEPTIDE PRODUCTION

CROSS REFERENCES TO RELATED APPLICATIONS

This application is a continuation of U.S. application Ser. No. 14/211,416, filed Mar. 14, 2014, now U.S. Pat. No. 10,017,732, issued Jul. 10, 2018, which claims the priority benefit of U.S. Provisional Application Ser. No. 61/799,602, filed Mar. 15, 2013, the contents of each of which are incorporated herein by reference in their entirety.

FIELD OF THE INVENTION

The present invention relates to cell culture media comprising antioxidants, methods of using the media for cell culture and polypeptide production as well as compositions and kits comprising the polypeptides produced by the methods provided herein.

BACKGROUND OF THE INVENTION

Cell culture manufacturing technology is widely used for the production of protein-based products such as pharmaceutical formulations of therapeutic proteins. Commercial production of protein-based products, such as an antibody product, requires optimization of cell culture parameters in order for the cell to produce enough of the protein product to meet manufacturing demands. However, when cell culture parameters are optimized for improving productivity of the protein product it is also necessary to maintain the desired quality attributes of the product such as the glycosylation profile, aggregate levels, charge heterogeneity, and amino acid sequence integrity (Li et al., *mAbs*, 2010, 2(5): 466-477). Another quality attribute of concern is the color of the protein product. Regulatory requirements regarding acceptable color levels for liquid formulations of therapeutic products for human use must be met (*United States Pharmacopoeia Inc.*, 2000, p. 1926-1927 and Council of Europe. *European Pharmacopoeia*, 2008, 7$^{th}$ Ed. p. 22). Thus, producing a protein product that has an acceptable color is an important aspect of therapeutic protein production.

Recent trends towards the subcutaneous delivery of therapeutic proteins, such as monoclonal antibodies, has been accompanied by an increase in concentration of the formulated protein substance, for example at concentrations about 100 mg/mL or greater (Daugherty et al., *Adv Drug Deliver Rev*, 2006, 58(5-6):686-706). A correlation between increased color intensity in compositions comprising increasing amounts of therapeutic protein has been observed and this relationship may be due low-level protein product variants previously unobservable by standard methods for monitoring color intensity of the formulated product.

Oxidation is a major chemical degradation pathway for protein pharmaceuticals. For example, methionine, cysteine, histidine, tryptophan, and tyrosine are amino acid residues that are susceptible to oxidation due to their reactivity with reactive oxygen species (ROS) and this oxidation is often observed in pharmaceutical protein formulations during storage. Although it is known that cell culture conditions can impact quality attributes of the protein product, such as production of sufficient amounts for large-scale manufacturing, the impact of these conditions on the color intensity of the final protein product remains unclear.

There is a continuing need to provide improved and cost-effective methods of producing proteins (e.g., antibodies) having acceptable product quality attributes such as color intensity. Cell culture media, whether chemically undefined or chemically defined, having components that consistently deliver protein products at lower color intensities while maintaining a desired protein concentration (e.g., ≥100 mg/mL) would find use in the development of protein products, such as antibodies.

BRIEF SUMMARY OF THE INVENTION

In some aspects, the invention herein provides a method of culturing a cell comprising a nucleic acid encoding a polypeptide, wherein the method comprises the step of contacting the cell with a cell culture medium comprising hypotaurine or an analog or precursor thereof, wherein the cell culture medium comprising the hypotaurine or an analog of precursor thereof reduces the color intensity of a composition comprising the polypeptide produced by the cell as compared to the color intensity of a composition comprising the polypeptide produced by the cell cultured in a cell culture medium that does not comprise the hypotaurine or an analog or precursor thereof. In some embodiments, the cell culture medium comprising the hypotaurine or an analog or precursor thereof reduces the color intensity of a composition comprising the polypeptide produced by the cell by at least about 0.1% as compared to a composition comprising the polypeptide produced by the cell cultured in a cell culture medium that does not comprise the hypotaurine or an analog or precursor thereof. In some embodiments, the cell culture medium comprising the hypotaurine or an analog or precursor thereof reduces the color intensity of a composition comprising the polypeptide produced by the cell by about 5% to about 50% as compared to a composition comprising the polypeptide produced by the cell cultured in a cell culture medium that does not comprise the hypotaurine or an analog or precursor thereof. In some of the embodiments herein, the cell culture medium comprises the hypotaurine or an analog or precursor thereof at a concentration of at least about 0.0001 mM. In some of the embodiments herein, the cell culture medium comprises the hypotaurine or an analog or precursor thereof at a concentration from about 0.0001 mM to about 500.0 mM. In some of the embodiments herein, the cell culture medium comprises the hypotaurine or an analog or precursor thereof at a concentration from about 1.0 mM to about 40.0 mM. In some of the embodiments herein, the cell culture medium comprises the hypotaurine or an analog or precursor thereof at a concentration from about 1.0 mM to about 10.0 mM. In some of the embodiments herein, the hypotaurine or an analog or precursor thereof is selected from the group consisting of hypotaurine, s-carboxymethylcysteine, cysteamine, cysteinesulphinic acid, and taurine. In some of the embodiments herein, the cell culture medium comprising the hypotaurine or an analog or precursor thereof is a chemically defined cell culture medium. In some of the embodiments herein, the cell culture medium comprising the hypotaurine or an analog or precursor thereof is a chemically undefined cell culture medium. In some of the embodiments herein, the cell culture medium comprising the hypotaurine or an analog or precursor thereof is a basal cell culture medium. In some of the embodiments herein, the cell culture medium comprising the hypotaurine or an analog or precursor thereof is a feed cell culture medium. In some of the embodiments herein, the cell is contacted with the cell culture medium comprising the hypotaurine or an analog or precursor thereof during the cell's growth phase. In some of the embodiments herein, the cell is contacted with the cell culture medium comprising the hypotaurine or an analog or precursor thereof during the cell's production phase. In some of the embodiments herein, the hypotaurine or an analog or precursor thereof is added to the cell culture medium on at least one day of a cell culture cycle. In some of the embodiments herein, the hypotaurine or an analog or precursor thereof is added to the cell culture medium on day 0 of a 14 day cell culture cycle. In any of the embodiments herein, the hypotaurine or an analog or precursor thereof can be added to the cell culture medium on any day of a cell culture cycle. In some of the embodiments herein, the cell is a mammalian cell. In some of the embodiments herein, the mammalian cell is a Chinese Hamster Ovary (CHO) cell. In some of the embodiments herein, the polypeptide is an antibody or fragment thereof.

In other aspects, the invention herein provides methods of culturing a cell comprising a nucleic acid encoding a polypeptide, wherein the method comprises the step of contacting the cell with a cell culture medium, wherein the cell culture medium comprises one or more of components (a)-(g): (a) hypotaurine; (b) s-carboxymethylcysteine; (c) carnosine; (d) anserine; (e) butylated hydroxyanisole; (f) lipoic acid; and (g) quercitrin hydrate, and wherein the cell culture medium comprising one or more of components (a)-(g) reduces the color intensity of a composition comprising the polypeptide produced by the cell as compared to a composition comprising the polypeptide produced by the cell cultured in a cell culture medium that does not comprise the one or more of components (a)-(g). In some embodiments, the cell culture medium comprising one or more of components (a)-(g) reduces the color intensity of a composition comprising the polypeptide produced by the cells by at least about 0.1% as compared to a composition comprising the polypeptide produced by the cell cultured in a cell culture medium that does not comprise the one or more of components (a)-(g). In some embodiments, the cell culture medium comprising one or more of components (a)-(g) reduces the color intensity of a composition comprising the polypeptide produced by the cells by about 5% to about 50% as compared to a composition comprising the polypeptide produced by the cell cultured in a cell culture medium that does not comprise the one or more of components (a)-(g). In some of the embodiments herein, the cell culture medium comprising one or more of components (a)-(g) comprises the one or more components (a)-(g) in an amount selected from: (a) hypotaurine at a concentration from at least about 0.0001 mM; (b) s-carboxymethylcysteine at a concentration from at least about 0.0001 mM; (c) carnosine at a concentration from at least about 0.0001 mM; (d) anserine at a concentration from at least about 0.0001 mM; (e) butylated hydroxyanisole at a concentration from at least about 0.0001 mM; (f) lipoic acid at a concentration from at least about 0.0001 mM; and (g) quercitrin hydrate at a concentration from at least about 0.0001 mM. In a further embodiment, the cell culture medium comprises hypotaurine at a concentration from about 2.0 mM to about 50.0 mM. In some of the embodiments herein, the cell culture medium comprises s-carboxymethylcysteine at a concentration from about 8.0 mM to about 12.0 mM. In some of the embodiments herein, the cell culture medium comprises carnosine at a concentration from about 8.0 mM to about 12.0 mM. In some of the embodiments herein, the cell culture medium comprises anserine at a concentration from about 3.0 mM to about 5.0 mM. In some of the embodiments herein, the cell culture medium comprises butylated hydroxyanisole at a concentration from about 0.025 mM to about 0.040 mM. In some of the embodiments herein, the cell culture medium comprises lipoic acid at a concentration from about 0.040 mM to about 0.060 mM. In some of the embodiments herein, the cell culture medium comprises quercitrin hydrate at a concentration from about 0.010 mM to about 0.020 mM. In some of the embodiments herein, the cell culture medium is a chemically defined cell culture medium. In some of the embodiments herein, the cell culture medium is a chemically undefined cell culture medium. In some of the embodiments herein, the cell culture medium is a basal cell culture medium. In some of the embodiments herein, the cell culture medium is a feed cell culture medium. In some of the embodiments herein, the cell is contacted with the cell culture medium during the cell's growth phase. In some of the embodiments herein, the cell is contacted with the cell culture medium during the cell's production phase. In some of the embodiments herein, the one or more of components (a)-(g) is added to the cell culture medium on at least one day of a cell culture cycle. In some of the embodiments herein, the one or more of components (a)-(g) is added to the cell culture medium on day 0 of a 14 day cell culture cycle. In any of the embodiments herein, the one or more of components (a)-(g) can be added to the cell culture medium on any day of a cell culture cycle. In some of the embodiments herein, wherein the cell is a mammalian cell. In some of the embodiments herein, wherein the mammalian cell is a Chinese Hamster Ovary (CHO) cell. In some of the embodiments herein, wherein the polypeptide is an antibody or fragment thereof.

In some aspects, the invention herein also provides methods of producing a polypeptide comprising the step of culturing a cell comprising a nucleic acid encoding the polypeptide in a cell culture medium comprising hypotaurine or an analog or precursor thereof, and wherein the cell culture medium comprising the hypotaurine or an analog or precursor thereof reduces the color intensity of a composition comprising the polypeptide produced by the cell as compared to the color intensity of a composition comprising the polypeptide produced by the cell cultured in a cell culture medium that does not comprise the hypotaurine or an analog or precursor thereof. In some embodiments, the cell culture medium comprising the hypotaurine or an analog or precursor thereof reduces the color intensity of a composition comprising the polypeptide produced by the cell by at least about 0.1% as compared to a composition comprising the polypeptide produced by the cell cultured in a cell culture medium that does not comprise the hypotaurine or an analog or precursor thereof. In some embodiments, the cell culture medium comprising the hypotaurine or an analog or precursor thereof reduces the color intensity of a composition comprising the polypeptide produced by the cell by about 5% to about 50% as compared to a composition comprising the polypeptide produced by the cell cultured in a cell culture medium that does not comprise the hypotaurine or an analog or precursor thereof. In some of the embodiments herein, the cell culture medium comprises the hypotaurine or an analog or precursor thereof at a concentration from at least about 0.0001 mM. In some of the embodiments herein, the cell culture medium comprising comprises the hypotaurine or an analog or precursor thereof at a concentration from about 0.0001 mM to about 500.0 mM. In some of the embodiments herein, the cell culture medium comprises the hypotaurine or an analog or precursor thereof at a concentration from about 1.0 mM to about 40.0 mM. In some of the embodiments herein, the cell culture medium comprises the hypotaurine or an analog or precursor thereof at a concentration from about 1.0 mM to about 10.0 mM. In some of the embodiments herein, the hypotaurine or an analog or precursor thereof is selected from the group consisting of hypotaurine, s-carboxymethylcysteine, cysteamine, cysteinesulphinic acid, and taurine. In some of the embodiments herein, the cell culture medium is a chemically defined cell culture medium. In some of the embodiments herein, the cell culture medium is a chemically undefined cell culture medium. In some of the embodiments herein, the cell culture medium is a basal cell culture medium. In some of the embodiments herein, the cell culture medium is a feed cell culture medium. In some of the embodiments herein, the hypotaurine or an analog or precursor thereof is added to the cell culture medium on at least one day of a cell culture cycle. In some of the embodiments herein, the hypotaurine or an analog or precursor thereof is added to the cell culture medium on day 0 of a 14 day cell culture cycle. In any of the embodiments herein, the hypotaurine or an analog or precursor thereof can be added to the cell culture medium on any day of a cell culture cycle. In some of the embodiments herein, the cell is a mammalian cell. In some embodiments, the mammalian cell is a Chinese Hamster Ovary (CHO) cell. In some of the embodiments herein, the polypeptide is an antibody. In some embodiments, the antibody is an IgG1 antibody. In some embodiments, the antibody is secreted into the cell culture medium comprising the hypotaurine or an analog or precursor thereof. In some embodiments, the method further comprises the step of recovering the polypeptide from the cell culture medium comprising the hypotaurine or an analog or precursor thereof. In some embodiments, the composition comprising the recovered polypeptide is a liquid composition or a non-liquid composition. In some embodiments, the composition comprising the recovered polypeptide appears as a colorless or slightly colored liquid.

In some aspects, the invention provides a method of producing a polypeptide comprising the step of culturing a cell comprising a nucleic acid encoding the polypeptide in a cell culture medium, wherein the cell culture medium comprises one or more of components (a)-(g): (a) hypotaurine; (b) s-carboxymethylcysteine; (c) carnosine; (d) anserine; (e) butylated hydroxyanisole; (f) lipoic acid; and (g) quercitrin hydrate, and wherein the cell culture medium comprising one or more of components (a)-(g) reduces the color intensity of a composition comprising the polypeptide produced by the cell as compared to a composition comprising the polypeptide produced by the cell cultured in a cell culture medium that does not comprise one or more of components (a)-(g). In some embodiments, the cell culture medium comprising one or more of components (a)-(g) reduces the color intensity of a composition comprising the polypeptide produced by the cells by at least about 0.1% as compared to a composition comprising the polypeptide produced by the cell cultured in a cell culture medium that does not comprise the one or more of components (a)-(g). In some embodiments, the cell culture medium comprising one or more of components (a)-(g) reduces the color intensity of a composition comprising the polypeptide produced by the cells by about 5% to about 50% as compared to a composition comprising the polypeptide produced by the cell cultured in a cell culture medium that does not comprise the one or more of components (a)-(g). In some of the embodiments herein, the cell culture medium comprises the one or more components (a)-(g) in an amount selected from: (a) hypotaurine at a concentration from at least about 0.0001 mM; (b) s-carboxymethylcysteine at a concentration from at least about 0.0001 mM; (c) carnosine at a concentration from at least about 0.0001 mM; (d) anserine at a concentration from at least about 0.0001 mM; (e) butylated hydroxyanisole at a concentration from at least about 0.0001 mM; (f) lipoic acid at a concentration from at least about 0.0001 mM; and (g) quercitrin hydrate at a concentration from at least about 0.0001 mM. In some embodiments, the cell culture medium comprises hypotaurine at a concentration from about 2.0 mM to about 50.0 mM. In some of the embodiments herein, the cell culture medium comprises s-carboxymethylcysteine at a concentration from about 8.0 mM to about 12.0 mM. In some of the embodiments herein, the cell culture medium comprises carnosine at a concentration from about 8.0 mM to about 12.0 mM. In some of the embodiments herein, the cell culture medium comprises anserine at a concentration from about 3.0 mM to about 5.0 mM. In some of the embodiments herein, the cell culture medium comprises butylated hydroxyanisole at a concentration from about 0.025 mM to about 0.040 mM. In some of the embodiments herein, the cell culture medium comprises lipoic acid at a concentration from about 0.040 mM to about 0.060 mM. In some of the embodiments herein, the cell culture medium comprises quercitrin hydrate at a concentration from about 0.010 mM to about 0.020 mM. In some of the embodiments herein, the cell culture medium is a chemically defined cell culture medium. In some of the embodiments herein, the cell culture medium is a chemically undefined cell culture medium. In some of the embodiments herein, the cell culture medium is a basal cell culture medium. In some of the embodiments herein, the cell culture medium is a feed cell culture medium. In some of the embodiments herein, the cell is contacted with the cell culture medium during the cell's growth phase. In some of the embodiments herein, the cell is contacted with the cell culture medium during the cell's production phase. In some of the embodiments herein, the one or more of components (a)-(g) is added to the cell culture medium on at least one day of a cell culture cycle. In some of the embodiments herein, the one or more of components (a)-(g) is added to the cell culture medium on day 0 of a 14 day cell culture cycle. In any of the embodiments herein, the one or more of components (a)-(g) can be added to the cell culture medium on any day of a cell culture cycle. In some of the embodiments herein, the cell is a mammalian cell. In some embodiments, the mammalian cell is a Chinese Hamster Ovary (CHO) cell. In some of the embodiments herein, the polypeptide is an antibody or fragment thereof. In some embodiments, the antibody is an IgG1 antibody. In some embodiments, the antibody is secreted into the cell culture medium. In some of the embodiments herein, the method further comprises the step of recovering the polypeptide from the cell culture medium comprising one or more of components (a)-(g). In some embodiments, a composition comprising the recovered polypeptide is a liquid composition or a non-liquid composition. In some embodiments, the composition comprising the recovered polypeptide appears as a colorless or slightly colored liquid. In some of the embodiments herein, a polypeptide can be produced by the any of the methods described herein.

In some aspects, the invention provides a pharmaceutical composition comprising a polypeptide produced by any of the methods described herein and a pharmaceutically acceptable carrier.

In some aspects, the invention provides a kit for supplementing a cell culture medium with chemically defined constituents, the kit comprising hypotaurine or an analog or precursor thereof at a concentration of at least about 0.0001 mM, and wherein the hypotaurine or an analog or precursor is selected from the group consisting of hypotaurine, s-carboxymethylcysteine, cysteamine, cysteinesulphinic acid, and taurine.

In other aspects, the invention also provides a kit for supplementing a cell culture medium with chemically defined constituents, the kit comprising one or more of: (a) hypotaurine in an amount to provide from at least about 0.0001 mM hypotaurine in the cell culture medium; (b) s-carboxymethylcysteine in an amount to provide from at least about 0.0001 mM s-carboxymethylcysteine in the cell culture medium; (c) carnosine in an amount to provide from at least about 0.0001 mM carnosine in the cell culture medium; (d) anserine in an amount to provide from at least about 0.0001 mM anserine in the cell culture medium; (e) butylated hydroxyanisole in an amount to provide from at least about 0.0001 mM butylated hydroxyanisole; (f) lipoic acid in an amount to provide from at least about 0.0001 mM lipoic acid in the cell culture medium; and (g) quercitrin hydrate in an amount to provide from at least about 0.0001 mM quercitrin hydrate in the cell culture medium.

In some aspects, the invention herein provides a cell culture medium comprising from at least about 0.0001 mM of hypotaurine or an analog or precursor thereof selected from the group consisting of hypotaurine, s-carboxymethylcysteine, cysteamine, cysteinesulphinic acid, and taurine.

In other aspects of the invention, provided herein is a cell culture medium comprising one or more of components (a)-(g): (a) from at least about 0.0001 mM hypotaurine; (b) from at least about 0.0001 mM s-carboxymethylcysteine; (c) from at least about 0.0001 mM carnosine; (d) from at least about 0.0001 mM anserine; (e) from at least about 0.0001 mM butylated hydroxyanisole; (f) from at least about 0.0001 mM lipoic acid; and (g) from at least about 0.0001 mM quercitrin hydrate.

In some aspects, the invention herein provides a composition comprising (a) a cell comprising a nucleic acid encoding a polypeptide; and (b) any cell culture medium described herein.

In some aspects of the invention, provided herein is a composition comprising: (a) a polypeptide; and (b) any cell culture medium described herein. In some embodiments, the polypeptide is secreted into the cell culture medium by a cell comprising a nucleic acid encoding the polypeptide.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

DETAILED DESCRIPTION

I. Definitions

Figure 1:
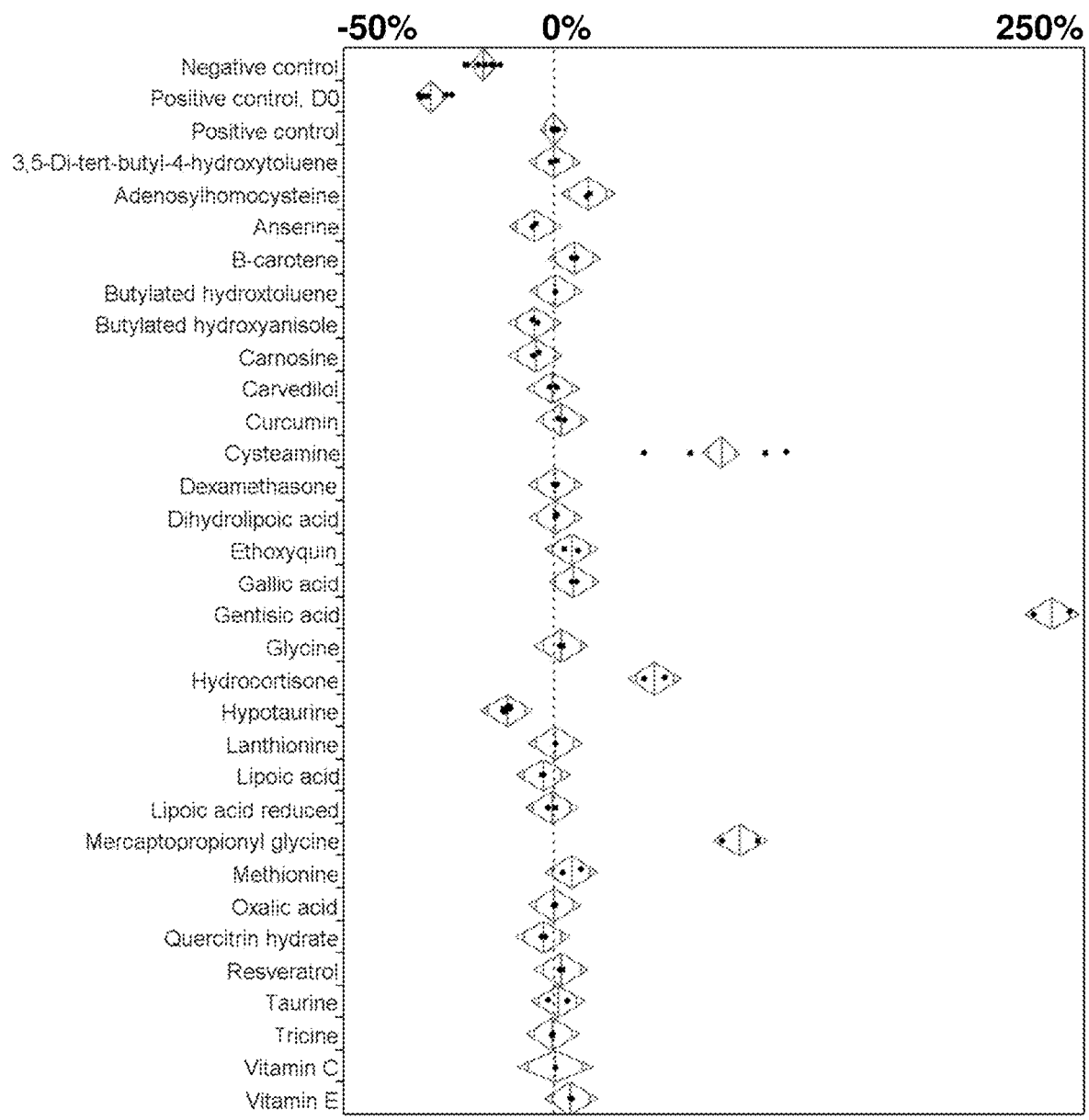
FIG. 1 is a graph of representative compounds screened for impact on color intensity in a representative cell culture medium containing an antibody. Numerical results were normalized to the positive control where the value for the positive control was set at 0% change in color intensity. Values higher than 0% indicate increased color intensity. Values lower than 0% indicate reduced color intensity.

The terms "medium" and "cell culture medium" refer to a nutrient source used for growing or maintaining cells. As is understood by a person of skill in the art, the nutrient source may contain components required by the cell for growth and/or survival or may contain components that aid in cell growth and/or survival. Vitamins, essential or non-essential amino acids, and trace elements are examples of medium components.

A "chemically defined cell culture medium" or "CDM" is a medium with a specified composition that is free of products derived from animal or plant such as for example animal serum and plant peptone. As would be understood by a person of skill in the art, a CDM may be used in a process of polypeptide production whereby a cell is in contact with, and secretes a polypeptide into, the CDM. Thus, it is understood that a composition may contain a CDM and a polypeptide product and that the presence of the polypeptide product does not render the CDM chemically undefined.

A "chemically undefined cell culture medium" refers to a medium whose chemical composition cannot be specified and which may contain one or more products derived from animal or plant such as for example animal serum and plant peptone. As would be understood by a person of skill in the art, a chemically undefined cell culture medium may contain a product derived from an animal or a plant as a nutrient source.

"Culturing" a cell refers to contacting a cell with a cell culture medium under conditions suitable to the survival and/or growth and/or proliferation of the cell.

"Batch culture" refers to a culture in which all components for cell culturing (including the cells and all culture nutrients) are supplied to the culturing vessel at the start of the culturing process.

The phrase "fed batch cell culture," as used herein refers to a batch culture wherein the cells and culture medium are supplied to the culturing vessel initially, and additional culture nutrients are fed, continuously or in discrete increments, to the culture during the culturing process, with or without periodic cell and/or product harvest before termination of culture.

"Perfusion culture" is a culture by which the cells are restrained in the culture by, e.g., filtration, encapsulation, anchoring to microcarriers, etc., and the culture medium is continuously or intermittently introduced and removed from the culturing vessel.

"Culturing vessel" refers to a container used for culturing a cell. The culturing vessel can be of any size so long as it is useful for the culturing of cells.

As used herein, "hypotaurine analog" refers to a chemical compound that is structurally similar to hypotaurine, but differs from hypotaurine in chemical composition (e.g., differs by the number, location or chemical nature of functional groups or substituents on the hypotaurine core). The hypotaurine analog may or may not have different chemical or physical properties than hypotaurine and may or may not have improved activity in cell culture media as compared to hypotaurine, e.g., further reducing the color intensity of a polypeptide (e.g., an antibody) produced in the cell culture media as compared to hypotaurine. For example, the hypotaurine analog may be more hydrophilic or it may have altered reactivity as compared to hypotaurine. The hypotaurine analog may mimic the chemical and/or biologically activity of hypotaurine (i.e., it may have similar or identical activity), or, in some cases, may have increased or decreased activity as compared to hypotaurine.

The term "titer" as used herein refers to the total amount of recombinantly expressed polypeptide produced by a cell culture divided by a given amount of medium volume. Titer is typically expressed in units of milligrams of polypeptide per milliliter of medium.

A "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

An "isolated nucleic acid" means and encompasses a non-naturally occurring, recombinant or a naturally occurring sequence outside of or separated from its usual context. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the protein where, for example, the nucleic acid molecule is in a chromosomal location different from that of natural cells.

An "isolated" protein (e.g., an isolated antibody) is one which has been identified and separated and/or recovered from a component of its natural environment. Contaminant components of its natural environment are materials which would interfere with research, diagnostic or therapeutic uses for the protein, and may include enzymes, hormones, and other proteinaceous or nonproteinaceous solutes. Isolated protein includes the protein in situ within recombinant cells since at least one component of the protein's natural environment will not be present. Ordinarily, however, isolated protein will be prepared by at least one purification step.

A "purified" polypeptide means that the polypeptide has been increased in purity, such that it exists in a form that is more pure than it exists in its natural environment and/or when initially produced and/or synthesized and/or amplified under laboratory conditions. Purity is a relative term and does not necessarily mean absolute purity.

"Contaminants" refer to materials that are different from the desired polypeptide product. The contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Examples of polypeptides encompassed within the definition herein include mammalian proteins, such as, e.g., renin;

a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. An antibody can be human, humanized and/or affinity matured.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies to be used in accordance with the invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods in bacterial, eukaryotic animal or plant cells (see, e.g., U.S. Pat. No. 4,816,567); phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004) and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

"Pharmaceutically acceptable" carriers, excipients, or stabilizers are ones which are nontoxic to the cell or mammal being exposed thereto at the dosages and concentrations employed (Remington's Pharmaceutical Sciences (20$^{th}$ edition), ed. A. Gennaro, 2000, Lippincott, Williams & Wilkins, Philadelphia, Pa.). Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™.

A "sterile" formulation is aseptic or free or essentially free from all living microorganisms and their spores.

A "colorless or slightly colored" liquid refers to a liquid composition comprising a polypeptide that is measured by quantitative and/or qualitative analysis. Qualitative analysis includes visual inspection such as comparison of the composition comprising the polypeptide to a reference standard.

As used in this specification and the appended claims, the singular forms "a", "an" and "the" include plural referents unless the content clearly dictates otherwise. Thus, for example, reference to "a compound" optionally includes a combination of two or more such compounds, and the like.

It is understood that aspect and embodiments of the invention described herein include "comprising," "consisting," and "consisting essentially of" aspects and embodiments.

Reference to "about" a value or parameter herein includes (and describes) embodiments that are directed to that value or parameter per se. For example, description referring to "about X" includes description of "X." Numeric ranges are inclusive of the numbers defining the range.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

II. Cell Culture Media

Cell culture media provided herein may find use in methods (e.g., of culturing cells and producing polypeptides) and in compositions (e.g., pharmaceutical formulations) as detailed herein. Media components have been identified as capable of providing a polypeptide product (e.g., a therapeutic protein) with acceptable quality attributes, such as an acceptable color intensity. One or more of these identified media components can be used to provide a polypeptide product with an acceptable color intensity. As used herein, "an acceptable color intensity" of a polypeptide product (e.g., composition comprising the polypeptide) can refer to the color intensity required for regulatory approval of the polypeptide product or the color intensity desired for use in assessing consistency in lot to lot batches of the polypeptide product. In some embodiments, the one or more media component is an antioxidant. In some embodiments, the one or more media component is selected from the group consisting of hypotaurine, s-carboxymethylcysteine, anserine, butylated hydroxyanisole, carnosine, lipoic acid, and quercitrin hydrate. In some embodiments, the one or more media component is hypotaurine or an analog or precursor thereof. In some embodiments, the hypotaurine or an analog or precursor thereof is selected from the group consisting of hypotaurine, s-carboxymethylcysteine, cysteamine, cysteinesulphinic acid, and taurine. In some embodiments, the one or more media component is taurine, lipoic acid reduced, or carvedilol.

Media components may be added to the cell culture media in forms that are known in the art. For example, hypotaurine may be provided as a compound identified by CAS number 300-84-5, s-carboxymethylcysteine may be provided as a compound identified by CAS number 638-23-3, anserine may be provided as a compound identified by CAS number 10030-52-1, butylated hydroxyanisole may be provided as a compound identified by CAS number 25013-16-5, carnosine may be provided as a compound identified by CAS number 305-84-0, lipoic acid may be provided as a compound identified by CAS number 1200-22-2, quercitrin hydrate may be provided as a compound identified by CAS number 522-12-3. As another example, analogs or precursors of hypotaurine may be provided such as s-carboxymethylcysteine, cysteamine, cysteinesulphinic acid, and/or taurine. In some embodiments, s-carboxymethylcysteine is provided as a compound identified by CAS number 638-23-3, cysteamine is provided as a compound identified by CAS number 60-23-1, cysteinesulphinic acid is provided as a compound identified by CAS number 1115-65-7, and taurine is provided as a compound identified by CAS number 107-35-7. In some embodiments, a compound listed in Table 4 is provided such as lipoic acid reduced identified by CAS number 462-20-4 or carvedilol identified by CAS number 72956-09-3. The media components provided herein can be provided to the cell culture medium as a salt, a hydrate, or a salt hydrate or any other form known to one of skill in the art. The media components can also be provided to cell culture media as a solution, an extract, or in solid form. In some embodiments herein, the cell culture medium is a chemically defined medium. In other embodiments herein, the cell culture medium is a chemically undefined medium.

In some aspects, the invention herein provides a cell culture medium comprising one or more of the following components: (a) hypotaurine; (b) s-carboxymethylcysteine; (c) carnosine; (d) anserine; (e) butylated hydroxyanisole; (f) lipoic acid; and (g) quercitrin hydrate. In some embodiments, the cell culture medium comprises 2 or 3 or 4 or 5 or 6 or each of components (a), (b), (c), (d), (e), (f) and (g). It is understood that the cell culture medium provided herein may contain any combination of components (a), (b), (c), (d), (e), (f) and (g) the same as if each and every combination were specifically and individually listed. For example, it is understood that a cell culture medium comprising four of components (a), (b), (c), (d), (e), (f) and (g) may comprise any combination of the components so long as at least four of the components are present.

In some aspects, a cell culture medium as provided herein contains one or more media components selected from the group consisting of (a) hypotaurine; (b) s-carboxymethylcysteine; (c) carnosine; (d) anserine; (e) butylated hydroxyanisole; (f) lipoic acid; and (g) quercitrin hydrate in amounts as described in Table 1. It is understood that a medium may comprise any one or more of the medium components of Table 1 (e.g., any one or more of components (a)-(g), such as a medium comprising components (a), (b), (c), (d) and (e) or a medium comprising components (a), (b) and (g) or a medium comprising only one of components (a)-(g)) in any of the amounts listed in Table 1, the same as if each and every combination of components and amounts were specifically and individually listed. In one aspect, the cell culture medium is a chemically defined medium. In another aspect, the cell culture medium is a chemically undefined medium. In some embodiments, a cell culture medium comprises one or more of components (a)-(g), wherein (a) is from at least about 0.0001 mM hypotaurine, (b) is from at least about 0.0001 mM s-carboxymethylcysteine, (c) is f from at least about 0.0001 mM carnosine, (d) is from at least about 0.0001 mM anserine, (e) is from at least about 0.0001 mM butylated hydroxyanisole, (f) is from at least about 0.0001 mM lipoic acid, and (g) is from at least about 0.0001 mM quercitrin hydrate. In some embodiments, a cell culture medium comprises one or more of components (a)-(g), wherein (a) is from about 2.0 mM to about 50.0 mM hypotaurine, (b) is from about 8.0 mM to about 12.0 mM s-carboxymethylcysteine, (c) is from about 8.0 mM to about 12.0 mM carnosine, (d) is from about 3.0 mM to about 5.0 mM anserine, (e) is from about 0.025 mM to about 0.040 mM butylated hydroxyanisole, (f) is from about 0.040 mM to about 0.060 mM lipoic acid, and (g) is from about 0.010 mM to about 0.020 mM quercitrin hydrate.

TABLE 1

Exemplary Amounts of Media Components

| Component | Amount of Component in Medium |
|---|---|
| (a) Hypotaurine | from about 0.0001 mM to about 920 mM; from about 0.001 mM to about 920 mM; from about 0.01 mM to about 920 mM; from about 0.1 mM to about 920 mM; from about 0.5 mM to about 920 mM; from about 0.0001 mM to about 820 mM; from about 0.0001 mM to about 720 mM; from about 0.0001 mM to about 620 mM; from about 0.0001 mM to about 520 mM; from about 0.0001 mM to about 420 mM; from about 0.0001 mM to about 320 mM; from about 0.0001 mM to about 220 mM; from about 0.0001 mM to about 120 mM; from about 0.0001 mM to about 20 mM; from about 1.0 mM to about 920 mM; from about 10.0 mM to about 920 mM; from about 20.0 mM to about 920 mM; from about 40.0 mM to about 920 mM; from about 80.0 mM to about 920 mM; from about 160.0 mM to about 920 mM; from about 320 mM to about 920 mM; from about 640 mM to about 920 mM; from about 800 mM to about 920 mM; from about 0.75 mM to about 700 mM; from about 1.0 mM to about 500 mM; from about 1.25 mM to about 300 mM; from about 1.5 mM to 100 mM; from about 1.6 mM to about 90 mM; from about 1.7 mM to about 80 mM; from about 1.8 mM to about 70 mM; from about 1.8 mM to about 60 mM; from about 1.8 mM to about 50 mM; from about 2 mM to about 50 mM; from about 5 mM to about 50 mM; from about 10 mM to about 50 mM; from about 15 mM to about 50 mM; from about 20 mM to about 50 mM; from about 30 mM to about 50 mM; from about 40 mM to about 50 mM; about any of 0.0001 or 0.001 or 0.01 or 0.1 or 1.0 or 2.0 or 3.0 or 4.0 or 5.0 or 9.0 or 12 or 25 or 38 or 45 or 50 mM; at least about any of 0.0001 or 0.001 or 0.01 or 0.1 or 1.0 or 2.0 or 3.0 or 4.0 or 5.0 or 9.0 or 12 mM and no more than about 60 or 55 or 50 or 45 or 40 mM. |
| (b) s-carboxymethyl cysteine | from about 0.0001 mM to about 120 mM; from about 0.001 mM to about 120 mM; from about 0.01 mM to about 120 mM; from about 0.1 mM to about 120 mM; from about 0.5 mM to about 120 mM; from about 0.0001 mM to 100 mM; from about 0.0001 mM to about 80 mM; from about 0.0001 mM to about 60 mM; from about 0.0001 mM to about 40 mM; from about 0.0001 mM to about 20 mM; from about 0.0001 mM to about 10 mM; from about 0.0001 mM to about 120 mM; from about 10 mM to about 120 mM; from about 20 mM to about 120 mM; from about 40 mM to about 120 mM; from about 60 mM to about 120 mM; from about 80 mM to about 120 mM; from about 100 mM to about 120 mM; from about 1.0 mM to about 100 mM; from about 2.0 mM to about 75 mM; from about 3.0 mM to about 50 mM; from about 4.0 mM to about 25 mM; from about 5.0 mM to about 15 mM; from about 6.0 mM to about 14 mM; from about 7.0 mM to about 13 mM; from about 8.0 mM to about 12 mM; about any of 0.0001 or 0.001 or 0.01 or 0.1 or 1.0 or 2.0 or 3.0 or 4.0 or 5.0 or 10 or 15 or 20 mM; at least about any of 0.0001 or 0.001 or 0.01 or 0.1 or 1.0 or 2.0 or 3.0 or 4.0 or 5.0 or 8.0 or 10 or 12 mM and no more than about 25 or 20 or 15 mM. |
| (c) Carnosine | from about 0.0001 mM to about 20 mM; from about 0.001 mM to about 20 mM; from about 0.01 mM to about 20 mM; from about 0.1 mM to about 20 mM; from about 0.5 mM to about 20 mM; from about 0.0001 mM to about 15 mM; from about 0.0001 mM to about 10 mM; from about 0.0001 mM to about 5.0 mM; from about 1.0 mM to about 20 mM; from about 5.0 mM to about 20 mM; from about 10 mM to about 20 mM; from about 15 mM to about 20 mM; from about 2.0 mM to about 18 mM; from about 4.0 mM to about 16 mM; from about 6.0 mM to about 14 mM; from about 8.0 mM to about 12 mM; about any of 0.0001 or 0.001 or 0.01 or 0.1 or 1.0 or 2.0 or 3.0 or 4.0 or 5.0 or 6.0 or 7.0 or 8.0 or 9.0 or 10 or 11 or 12 or 13 or 14 mM; at least about any of 0.0001 or 0.001 or 0.01 or 0.1 or 1.0 or 2.0 or 3.0 or 4.0 or 5.0 or 6.0 or 7.0 or 8.0 or 9.0 or 10 or 11 and no more than 15 or 14 or 13 mM. |
| (d) Anserine | from about 0.0001 mM to about 20 mM; from about 0.001 mM to about 20 mM; from about 0.01 mM to about 20 mM; from about 0.1 mM to about 20 mM; from about 0.5 mM to about 20 mM; from about 0.0001 mM to about 15 mM; from about 0.0001 mM to about 10 mM; from about 0.0001 mM to about 5.0 mM; from about 1.0 mM to about 20 mM; from about 5.0 mM to about 20 mM; from about 10 mM to about 20 mM; from about 15 mM to about 20 mM; from about 1.0 mM to about 15 mM; from about 2.0 mM to about 10 mM; from about 3.0 mM to about 5.0 mM; from about 3.2 mM to about 5.0 mM; about any of 0.0001 or 0.001 or 0.01 or 0.1 or 1.0 or 2.0 or 3.0 or 4.0 or 5.0 or 6.0 or 7.0 or 8.0 mM; at least about any of 0.0001 or 0.001 or 0.01 or 0.1 or 1.0 or 2.0 or 3.0 or 4.0 or 5.0 mM and no more than 9.0 or 8.0 or 7.0 or 6.0 mM. |
| (e) Butylated hydroxyanisole | from about 0.0001 mM to about 0.2 mM; from about 0.001 mM to about 0.2 mM; from about 0.005 mM to about 0.2 mM; from about 0.0001 mM to about 0.15 mM; from about 0.0001 mM to about 0.1 |

TABLE 1-continued

Exemplary Amounts of Media Components

| Component | Amount of Component in Medium |
|---|---|
| | mM; from about 0.0001 mM to about 0.05 mM; from about 0.0001 mM to about 0.04 mM; from about 0.01 mM to about 0.2 mM; from about 0.05 mM to about 0.2 mM; from about 0.1 mM to about 0.2 mM; from about 0.15 mM to about 0.2 mM; from about 0.01 mM to about 0.15 mM; from about 0.015 mM to about 0.1 mM; from about 0.02 mM to about 0.05 mM; from about 0.025 mM to about 0.04 mM; from about 0.03 mM to about 0.04 mM; about any of 0.0001 or 0.001 or 0.01 or 0.015 or 0.02 or 0.025 or 0.03 or 0.035 or 0.04 or 0.045 or 0.05 or 0.055 or 0.06 mM; at least about any of 0.0001 or 0.001 or 0.01 or 0.015 or 0.02 or 0.025 or 0.03 or 0.035 or 0.04 mM and no more than 0.06 or 0.055 or 0.05 mM. |
| (f) Lipoic acid | from about 0.0001 mM to about 1.5 mM; from about 0.001 mM to about 1.5 mM; from about 0.01 mM to about 1.5 mM; from about 0.0001 mM to about 1.25 mM; from about 0.0001 mM to about 1.0 mM; from about 0.0001 mM to about 0.75 mM; from about 0.0001 mM to about 0.5 mM; from about 0.0001 mM to about 0.25 mM; from about 0.05 mM to about 1.5 mM; from about 0.1 mM to about 1.5 mM; from about 0.25 mM to about 1.5 mM; from about 0.5 mM to about 1.5 mM; from about 0.75 mM to about 1.5 mM; from about 1.0 mM to about 1.5 mM; from about 1.25 mM to about 1.5 mM; from about 0.02 mM to about 1.25 mM; from about 0.03 mM to about 1.0 mM; from about 0.032 mM to about 0.1 mM; from about 0.034 mM to about 0.09 mM; from about 0.036 mM to about 0.08 mM; from about 0.038 mM to about 0.07 mM; from about 0.04 mM to about 0.06 mM; about any of 0.0001 or 0.001 or 0.01 or 0.02 or 0.03 or 0.04 or 0.05 or 0.06 or 0.07 or 0.08 or 0.09 mM; at least about any of 0.0001 or 0.001 or 0.01 or 0.02 or 0.03 or 0.04 or 0.05 mM and no more than 0.09 or 0.08 or 0.07 mM. |
| (g) Quercitrin hydrate | from about 0.0001 mM to about 0.04 mM; from about 0.001 mM to about 0.04 mM; from about 0.005 mM to about 0.04 mM; from about 0.001 mM to about 0.035 mM; from about 0.001 mM to about 0.03 mM; from about 0.001 mM to about 0.025 mM; from about 0.001 mM to about 0.02 mM; from about 0.001 mM to about 0.015 mM; from about 0.001 mM to about 0.01 mM; from about 0.01 mM to about 0.04 mM; from about 0.015 mM to about 0.04 mM; from about 0.02 mM to about 0.04 mM; from about 0.025 mM to about 0.04 mM; from about 0.03 mM to about 0.04 mM; from about 0.035 mM to about 0.04 mM; from about 0.0075 mM to about 0.035 mM; from about 0.01 mM to about 0.03 mM; from about 0.015 mM to about 0.025 mM; from about 0.01 mM to about 0.02 mM; about any of 0.0001 or 0.001 or 0.01 or 0.011 or 0.012 or 0.013 or 0.014 or 0.015 or 0.016 mM; at least about any of 0.0001 or 0.001 or 0.011 or 0.012 or 0.013 or 0.014 mM and no more than 0.02 or 0.019 or 0.018 mM. |

In some aspects, the invention herein provides a cell culture medium comprising hypotaurine or an analog or precursor thereof selected from the group consisting of hypotaurine, s-carboxymethylcysteine, cysteamine, cysteinesulphinic acid, and taurine. In some aspects, the cell culture medium comprises one or more of the following components: (a) hypotaurine; (b) s-carboxymethylcysteine; (c) cysteamine; (d) cysteinesulphinic acid; and (e) taurine. In some embodiments, the cell culture medium comprises 2 or 3 or 4 or each of components (a), (b), (c), (d), and (e). It is understood that the cell culture medium provided herein may contain any combination of components (a), (b), (c), (d), and (e) the same as if each and every combination were specifically and individually listed. For example, it is understood that a cell culture medium comprising three of components (a), (b), (c), (d), and (e) may comprise any combination of the components so long as at least three of the components are present. Hypotaurine analogs include for example s-carboxymethylcysteine, cysteamine, cysteinesulphinic acid, and taurine. Examples of hypotaurine precursors are well known to one of skill in the art and in some aspects a hypotaurine precursor can be a hypotaurine analog.

In some aspects, a cell culture medium as provided herein contains hypotaurine or an analog or precursor thereof in amounts as described in Table 2. It is understood that a medium may comprise any one or more of the medium components of Table 2 (e.g., any one or more of components (a)-(e), such as a medium comprising components (a), (b), (c), and (d) or a medium comprising components (a), (b) and (c) or a medium comprising only one of components (a)-(e)) in any of the amounts listed in Table 2, the same as if each and every combination of components and amounts were specifically and individually listed. In some embodiments, a cell culture medium comprises hypotaurine or an analog or precursor thereof such as hypotaurine, s-carboxymethylcysteine, cysteamine, cysteinesulphinic acid, and/or taurine at a concentration from at least about 0.0001 mM. In some embodiments, a cell culture medium comprises hypotaurine or an analog or precursor thereof such as hypotaurine, s-carboxymethylcysteine, cysteamine, cysteinesulphinic acid, and/or taurine at a concentration from about 0.5 mM to about 500.0 mM.

TABLE 2

Exemplary Amounts of Media Components

| Component | Amount of Component in Medium |
|---|---|
| (a) Hypotaurine | from about 0.0001 mM to about 920 mM; from about 0.001 mM to about 920 mM; from about 0.01 mM to about 920 mM; from about 0.1 mM to about 920 mM; from about 0.5 mM to about 920 mM; from about 0.0001 mM to about 820 mM; from about 0.0001 mM to about 720 mM; from about 0.0001 mM to about 620 mM; from about 0.0001 mM to about 520 mM; from about 0.0001 mM to about 420 mM; from about 0.0001 mM to about 320 mM; from about 0.0001 mM to about 220 mM; from about 0.0001 mM to about 120 mM; from about 0.0001 mM to about 20 mM; from about 1.0 mM to about 920 mM; from about 10.0 mM to about 920 mM; from about 20.0 mM to about 920 mM; from about 40.0 mM to about 920 mM; from about 80.0 mM to about 920 mM; from about 160.0 mM to about 920 mM; from about 320 mM to about 920 mM; from about 640 mM to about 920 mM; from about 800 mM to about 920 mM; from about 0.75 mM to about 700 mM; from about 1.0 mM to about 500 mM; from about 1.25 mM to about 300 mM; from about 1.5 mM to 100 mM; from about 1.6 mM to about 90 mM; from about 1.7 mM to about 80 mM; from about 1.8 mM to about 70 mM; from about 1.8 mM to about 60 mM; from about 1.8 mM to about 50 mM; from about 2 mM to about 50 mM; from about 5 mM to about 50 mM; from about 10 mM to about 50 mM; from about 15 mM to about 50 mM; from about 20 mM to about 50 mM; from about 30 mM to about 50 mM; from about 40 mM to about 50 mM; about any of 0.0001 or 0.001 or 0.01 or 0.1 or 1.0 or 2.0 or 3.0 or 4.0 or 5.0 or 9.0 or 12 or 25 or 38 or 45 or 50 mM; at least about any of 0.0001 or 0.001 or 0.01 or 0.1 or 1.0 or 2.0 or 3.0 or 4.0 or 5.0 or 9.0 or 12 mM and no more than about 60 or 55 or 50 or 45 or 40 mM. |
| (b) s-carboxymethyl cysteine | from about 0.0001 mM to about 120 mM; from about 0.001 mM to about 120 mM; from about 0.01 mM to about 120 mM; from about 0.1 mM to about 120 mM; from about 0.5 mM to about 120 mM; from about 0.0001 mM to 100 mM; from about 0.0001 mM to about 80 mM; from about 0.0001 mM to about 60 mM; from about 0.0001 mM to about 40 mM; from about 0.0001 mM to about 20 mM; from about 0.0001 mM to about 10 mM; from about 0.0001 mM to about 120 mM; from about 10 mM to about 120 mM; from about 20 mM to about 120 mM; from about 40 mM to about 120 mM; from about 60 mM to about 120 mM; from about 80 mM to about 120 mM; from about 100 mM to about 120 mM; from about 1.0 mM to about 100 mM; from about 2.0 mM to about 75 mM; from about 3.0 mM to about 50 mM; from about 4.0 mM to about 25 mM; from about 5.0 mM to about 15 mM; from about 6.0 mM to about 14 mM; from about 7.0 mM to about 13 mM; from about 8.0 mM to about 12 mM; about any of 0.0001 or 0.001 or 0.01 or 0.1 or 1.0 or 2.0 or 3.0 or 4.0 or 5.0 or 10 or 15 or 20 mM; at least about any of 0.0001 or 0.001 or 0.01 or 0.1 or 1.0 or 2.0 or 3.0 or 4.0 or 5.0 or 8.0 or 10 or 12 mM and no more than about 25 or 20 or 15 mM. |
| (c) cysteamine | from about 0.0001 mM to about 300 mM; from about 0.001 mM to about 300 mM; from about 0.01 mM to about 300 mM; from about 0.0001 mM to about 250 mM; from about 0.0001 mM to about 200 mM; from about 0.0001 mM to about 150 mM; from about 0.0001 mM to about 100 mM; from about 0.0001 mM to about 50 mM; from about 0.0001 mM to about 1 mM; from about 1 mM to about 300 mM; from about 50 mM to about 300 mM; from about 100 mM to about 300 mM; from about 150 mM to about 300 mM; from about 200 mM to about 300 mM; from about 250 mM to about 300 mM; from about 0.02 mM to about 300 mM; from about 0.03 mM to about 200 mM; from about 0.04 mM to about 100 mM; from about 0.05 mM to about 50 mM; from about 0.02 mM to about 1 mM; from about 0.04 mM to about 0.8 mM; from about 0.06 mM to about 0.6 mM; from about 0.08 mM to about 0.4 mM; from about 0.1 mM to about 0.2 mM; about any of 0.0001 or 0.001 or 0.01 or 0.02 or 0.05 or 0.1 or 0.25 or 0.5 or 1 or 5 or 10 or 25 or 50 or 100 or 200 or 300 mM; at least about 0.0001 or 0.001 or 0.01 or 0.02 or 0.05 or 0.1 or 0.25 mM and no more than about 50 or 40 or 30 mM. |
| (d) cysteinesulphinic acid | from about 0.0001 mM to 100 mM; from about 0.001 mM to 100 mM; from about 0.01 mM to 100 mM; from about 0.1 mM to 100 mM; from about 0.0001 mM to about 80 mM; from about 0.0001 mM to about 60 mM; from about 0.0001 mM to about 40 mM; from about 0.0001 mM to about 20 mM; from about 0.0001 mM to about 1 mM; from about 1 to 100 mM; from about 20 mM to about 100 mM; from about 40 mM to about 100 mM; from about 60 mM to about 100 mM; from about 80 mM to about 100 mM; from about 0.1 mM to about 50 mM; from about 0.2 mM to about 10 mM; from about 0.3 mM to about 1 mM; from about 0.1 mM to about 1 mM; from about 0.2 mM to about 0.8 mM; from about 0.3 mM to about 0.6 mM; about any of 0.0001 or 0.001 or 0.01 or 0.1 or 0.2 or 0.3 or 0.4 or 0.5 or 0.6 or 0.7 |

TABLE 2-continued

Exemplary Amounts of Media Components

| Component | Amount of Component in Medium |
|---|---|
| | or 1 or 10 or 25 or 50 or 100 mM; at least about 0.0001 or 0.001 or 0.01 or 0.1 or 0.1 or 0.2 or 0.3 or 0.4 mM and no more than 20 or 10 or 15 mM. |
| (e) taurine | from about 0.0001 mM to 500 mM; from about 0.001 mM to 500 mM; from about 0.01 mM to 500 mM; from about 0.1 mM to 500 mM; from about 0.5 mM to 500 mM; from about 0.0001 mM to about 450 mM; from about 0.0001 mM to about 400 mM; from about 0.0001 mM to about 350 mM; from about 0.0001 mM to about 300 mM; from about 0.0001 mM to 250 mM; from about 0.0001 mM to 200 mM; from about 0.0001 mM to 150 mM; from about 0.0001 mM to 100 mM; from about 0.0001 mM to about 50 mM; from about 1 mM to about 500 mM; from about 50 mM to about 500 mM; from about 100 mM to about 500 mM; from about 150 mM to about 500 mM; from about 200 mM to about 500 mM; from about 250 mM to about 500 mM; from about 300 mM to about 500 mM; from about 350 mM to about 500 mM; from about 400 mM to about 500 mM; from about 450 mM to about 500 mM; from about 1.0 mM to about 400 mM; from about 2.0 mM to about 300 mM; from about 3.0 mM to about 200 mM; from about 4.0 mM to about 100 mM; from about 1.0 mM to about 10 mM; about any of 0.0001 or 0.001 or 0.01 or 0.1 or 1or 2 or 3 or 4 or 5 or 6 or 7 or 8 or 9 mM; at least about any of 0.0001 or 0.001 or 0.01 or 0.1 or 1or 2 or 3 or 4 or 5 or 6 and no more than 13 or 12 or 11 mM. |

In some aspects, a cell culture medium provided herein comprises lipoic acid reduced at a concentration of about 0.0001 mM to about 0.5 mM. In some aspects, a cell culture medium provided herein comprises carvedilol at a concentration of about 0.0001 mM to about 1.5 mM.

Individual media components provided herein may be present in amounts that result in one or more advantageous properties for culturing cells and/or polypeptide production from cell culture. Advantageous properties include, but are not limited to, reduced oxidation of polypeptides in cell culture and/or reduced color intensity of a composition comprising a polypeptide produced by a cell cultured in a cell culture media provided herein. Advantageous properties of the cell culture media provided herein also include reduction of color intensity of a composition comprising a polypeptide produced by a cell cultured in the cell culture media without affecting one or more product attributes such as the amount of the polypeptide produced by the cells (e.g., antibody titer), the glycosylation (e.g., N-glycosylation) profile of the polypeptide, the polypeptide charge heterogeneity in the composition, or the amino acid sequence integrity of the polypeptide. In some embodiments, a one or more advantageous property for culturing a cell in a cell culture media provided herein is reduced color intensity of a composition comprising a polypeptide produced by the cell without affecting cell viability, the amount of the polypeptide produced by the cells, the glycosylation (e.g., N-glycosylation) profile of the polypeptide, the polypeptide charge heterogeneity in the composition, and/or the amino acid sequence integrity of the polypeptide. In some embodiments, a one or more advantageous property for culturing a cell in a cell culture media provided herein is reduced color intensity of a composition comprising a polypeptide produced by the cell and reduced oxidation of the polypeptide in cell culture. These advantageous properties are applicable to methods of culturing a cell comprising a nucleic acid encoding a polypeptide of interest and methods of producing a polypeptide of interest in cell culture as described herein.

In some aspects, one more media component selected from the group consisting of hypotaurine, s-carboxymethylcysteine, anserine, butylated hydroxyanisole, carnosine, lipoic acid, and quercitrin hydrate is provided herein in an amount that results in one or more advantageous property for culturing cells and/or polypeptide production from cell culture. In some embodiments, an amount of hypotaurine in cell culture media that results in one or more advantageous property is from about 0.5 mM to about 100 mM, from about 1.6 mM to about 90 mM, from about 1.7 mM to about 80 mM, from about 1.8 mM to about 70 mM, from about 1.9 mM to about 60 mM, from about 2.0 mM to about 50 mM, or from about 1.75 mM to about 50 mM. In some embodiments, an amount of s-carboxymethylcysteine in cell culture media that results in one or more advantageous property is from about 0.5 mM to about 120 mM, from about 5.0 mM to about 15 mM, from about 6.0 mM to about 14 mM, from about 7.0 mM to about 13 mM, or from about 8.0 mM to about 12 mM. In some embodiments, an amount of anserine in cell culture media that results in one or more advantageous property is from about 0.5 mM to about 20 mM, from about 2.0 mM to about 10 mM, or from about 3.0 mM to about 5.0 mM. In some embodiments, an amount of butylated hydroxyanisole in cell culture media that results in one or more advantageous property is from about 0.005 mM to about 0.2 mM, from about 0.02 mM to about 0.05 mM, or from about 0.025 mM to about 0.04 mM. In some embodiments, an amount of carnosine in cell culture media that results in one or more advantageous property is from about 0.5 mM to about 20 mM, from about 6.0 mM to about 14 mM, or from about 8.0 mM to about 12 mM. In some embodiments, an amount of lipoic acid in cell culture media that results in one or more advantageous property is from about 0.01 mM to about 1.5 mM lipoic acid, from about 0.036 mM to about 0.08 mM, from about 0.038 mM to about 0.07 mM or from about 0.04 mM to about 0.06 mM. In some embodiments, an amount of quercitrin hydrate in cell culture media that results in one or more advantageous property is from about 0.005 mM to about 0.04 mM, from about 0.01 mM to about 0.03 mM, from about 0.015 mM to about 0.025 mM or from about 0.01 mM to about 0.02 mM. In some embodiments, an amount of one more media component selected from the group consisting of hypotaurine, s-carboxymethylcysteine, anserine, butylated hydroxyanisole, carnosine, lipoic acid, and quercitrin hydrate in cell culture media that results in one or more advantageous property is provided in Table 1.

In some aspects, one more media component selected from the group consisting of hypotaurine, s-carboxymethylcysteine, cysteamine, cysteinesulphinic acid, and taurine is provided herein in an amount that results in one or more advantageous property for culturing cells and/or polypeptide production from cell culture. In some embodiments, an amount of hypotaurine in cell culture media that results in one or more advantageous property is from about 0.5 mM to about 100 mM, from about 1.6 mM to about 90 mM, from about 1.7 mM to about 80 mM, from about 1.8 mM to about 70 mM, from about 1.9 mM to about 60 mM, from about 2.0 mM to about 50 mM, or from about 1.75 mM to about 50 mM. In some embodiments, an amount of s-carboxymethylcysteine in cell culture media that results in one or more advantageous property is from about 0.5 mM to about 120 mM, from about 5.0 mM to about 15 mM, from about 6.0 mM to about 14 mM, from about 7.0 mM to about 13 mM, or from about 8.0 mM to about 12 mM. In some embodiments, an amount of cysteamine in cell culture media that results in one or more advantageous property is from about 0.01 mM to about 300 mM, from about 0.02 mM to about 1 mM, from about 0.04 mM to about 0.8 mM, from about 0.06 mM to about 0.6 mM, from about 0.08 mM to about 0.4 mM, or from about 0.1 mM to about 0.2 mM. In some embodiments, an amount of cysteinesulphinic acid in cell culture media that results in one or more advantageous property is from about 0.1 mM to 100 mM, from about 0.2 mM to about 10 mM, from about 0.3 mM to about 1 mM, from about 0.1 mM to about 1 mM, from about 0.2 mM to about 0.8 mM, or from about 0.3 mM to about 0.6 mM. In some embodiments, an amount of taurine in cell culture media that results in one or more advantageous property is from about 0.5 mM to 500 mM, from about 4.0 mM to about 100 mM, or from about 1.0 mM to about 10 mM. In some embodiments, an amount of one more media component selected from the group consisting of hypotaurine, s-carboxymethylcysteine, cysteamine, cysteinesulphinic acid, and taurine in cell culture media that results in one or more advantageous property is provided in Table 2.

A cell culture medium provided herein, in one aspect, results in one or more favorable product quality attributes or advantageous property when used in a method of producing a polypeptide in cell culture as compared to quality attributes of the polypeptide when produced in a different medium. Reactive oxygen species (ROS) formed through the use of certain media components may oxidize specific amino acids on the polypeptide and produce oxidized polypeptide products. The presence of such oxidized protein species may also alter the product quality attributes of a protein product, such as color intensity, which may be particularly significant for polypeptide products that are formulated at any concentration such as, but not limited to, a concentration of greater than any of about 1 mg/mL, about 10 mg/mL, about 25 mg/mL, about 50 mg/mL, or about 75 mg/mL up to 100 mg/mL. In some embodiments, the presence of oxidized protein species may alter the product quality attributes of a protein product, such as color intensity, which may be particularly significant for polypeptide products that are formulated at concentrations of greater than any of about 100 mg/mL, about 125 mg/mL, about 150 mg/mL, about 175 mg/mL, about 200 mg/mL or about 250 mg/mL. The color intensity of a composition comprising a polypeptide produced with a media detailed herein (including a composition comprising at least about 1 mg/mL, about 10 mg/mL, about 50 mg/mL, about 100 mg/mL, about 150 mg/mL, 200 mg/mL or about 250 mg/mL of the polypeptide, such as an antibody) can be assessed using a color assay such as one described herein or in, but not limited to, the United States Pharmacopoeia color standard and the European Pharmacopoeia color standard. See USP-24 Monograph 631 Color and Achromaticity. *United States Pharmacopoeia Inc.*, 2000, p. 1926-1927 and Council of Europe. *European Pharmacopoeia*, 2008, 7$^{th}$ Ed. P.22, which are incorporated herein by reference in their entirety. In any of the embodiments herein, a cell culture media provided herein can be used for the preparation of compositions comprising a polypeptide that have a reduced color intensity as compared to a reference solution as measured by a color assay. For example, the color intensity of a composition (e.g., pharmaceutical formulation) comprising a polypeptide (e.g., a therapeutic polypeptide) produced using a cell culture medium as provided herein can be reduced by any amount including, but not limited to, at least about 0.1%, 0.5%, 1%, 2%, 3%, 4%, 5% or more as compared to a composition comprising the polypeptide produced using a cell culture medium that does not comprise the one or more of components of Table 1 or Table 2.

Commercially available media such as, but not limited to, Ham's F10 (Sigma), Minimal Essential Medium ([MEM], Sigma), RPMI-1640 (Sigma), Dulbecco's Modified Eagle's Medium ([DMEM], Sigma), Luria broth (LB), and Terrific broth (TB) that are suitable for culturing cells may be supplemented with any of the media components as detailed herein (e.g., by use of a kit as provided). In addition, any of the media described in Ham and Wallace, Meth. Enz., 58:44 (1979), Barnes and Sato, Anal. Biochem., 102:255 (1980), Vijayasankaran et al., *Biomacromolecules.*, 6:605:611 (2005), Patkar et al., *J Biotechnology*, 93:217-229 (2002), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference in their entirety, may be supplemented with any of the media components as detailed herein (e.g., by use of a kit as provided).

In some embodiments, a cell culture medium provided herein comprises cystine and is free of cysteine. In some embodiments, a cell culture medium provided herein comprises ferric citrate and is free of ferrous sulfate. In some embodiments herein, a cell culture medium provided is free from cysteine and ferrous sulfate. In some embodiments, the medium is free from cysteine and ferrous sulfate and comprises cystine and/or ferric citrate. In any of the embodiments herein, the cell culture media can be a basal medium or a feed medium. Amino acids, vitamins, trace elements and other media components at one or two times the ranges specified in European Patent EP 307,247 or U.S. Pat. No. 6,180,401 may be used, which documents are herein incorporated by reference in their entireties.

Any media provided herein may also be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), and glucose or an equivalent energy source. In some aspects, a cell culture medium provided herein contains proteins derived from a plant or an animal. In some embodiments, a cell culture provided herein is free of proteins derived from a plant or an animal. Any other necessary supplements may also be included at appropriate concentrations that would be known to those skilled in the art.

III. Methods and Uses of the Invention

Provided herein are methods of culturing cells in a cell culture media provided herein for the production of polypeptides of interest. In some aspects, a method is provided for culturing a cell comprising a nucleic acid encoding a polypeptide of interest, wherein the method comprises the step of contacting the cell with a cell culture medium, wherein the cell culture medium comprises one or more of components selected from the group consisting of hypotaurine, s-carboxymethylcysteine, carnosine, anserine, butylated hydroxyanisole, lipoic acid, and quercitrin hydrate. In some embodiments, a method is provided for culturing a cell comprising a nucleic acid encoding a polypeptide of interest, wherein the method comprises the step of contacting the cell with a cell culture medium, wherein the cell culture medium comprises one or more of components selected from the group consisting of (a) hypotaurine, (b) s-carboxymethylcysteine, (c) carnosine, (d) anserine, (e) butylated hydroxyanisole, (f) lipoic acid; and (g) quercitrin hydrate, and wherein the cell culture medium comprising one or more of components (a)-(g) reduces the color intensity of a composition comprising the polypeptide produced by the cell as compared to a composition comprising the polypeptide produced by the cell cultured in a cell culture medium that does not comprise the one or more of components (a)-(g). In some embodiments, the color intensity of the composition comprising the polypeptide is reduced by at least about 0.1%. In some embodiments, the color intensity of the composition comprising the polypeptide is reduced by at least about 5%. In some embodiments, the color intensity of the composition comprising the polypeptide is reduced by about 10% to about 30%. In some of the embodiments herein, the cell culture medium comprises one or more components in an amount selected from (a) hypotaurine at a concentration from about 2.0 mM to about 50.0 mM, (b) s-carboxymethylcysteine at a concentration from about 8.0 mM to about 12.0 mM, (c) carnosine at a concentration from about 8.0 mM to about 12.0 mM, (d) anserine at a concentration from about 3.0 mM to about 5.0 mM, (e) butylated hydroxyanisole at a concentration from about 0.025 mM to about 0.040 mM, (f) lipoic acid at a concentration from about 0.040 mM to about 0.060 mM, and (g) quercitrin hydrate at a concentration from about 0.010 mM to about 0.020 mM. In some of the embodiments herein, the one or more components selected from the group consisting of (a) hypotaurine, (b) s-carboxymethylcysteine, (c) carnosine, (d) anserine, (e) butylated hydroxyanisole, (f) lipoic acid; and (g) quercitrin hydrate is added to the cell culture medium on day 0 of a 14 day cell culture cycle.

In some other aspects, a method is provided for culturing a cell comprising a nucleic acid encoding a polypeptide of interest, wherein the method comprises the step of contacting the cell with a cell culture medium comprising the hypotaurine or an analog or precursor thereof. In some embodiments, a method is provided for culturing a cell comprising a nucleic acid encoding a polypeptide of interest, wherein the method comprises the step of contacting the cell with a cell culture medium comprising the hypotaurine or an analog or precursor thereof, and wherein the cell culture medium comprising the hypotaurine or an analog or precursor thereof reduces the color intensity of a composition comprising the polypeptide produced by the cell as compared to the color intensity of a composition comprising the polypeptide produced by the cell cultured in a cell culture medium that does not comprise the hypotaurine or an analog or precursor thereof. In some embodiments, the color intensity of the composition comprising the polypeptide is reduced by at least about 0.1%. In some embodiments, the color intensity of the composition comprising the polypeptide is reduced by at least about 5%. In some embodiments, the color intensity of the composition comprising the polypeptide is reduced by about 10% to about 30%. In some embodiments herein, the cell culture medium comprises the hypotaurine or an analog or precursor thereof, at a concentration from at least about 0.0001 mM. In some embodiments herein, the cell culture medium comprises the hypotaurine or an analog or precursor thereof, at a concentration from about 0.5 mM to about 500 mM. In some embodiments, the cell culture medium comprises the hypotaurine or an analog or precursor thereof, at a concentration from about 1.0 mM to about 40 mM. In some embodiments herein, the hypotaurine or an analog or precursor thereof is selected from the group consisting of hypotaurine, s-carboxymethylcysteine, cysteamine, cysteinesulphinic acid, and taurine. In some of the embodiments herein, the hypotaurine or an analog or precursor thereof is added to the cell culture medium on day 0 of a 14 day cell culture cycle. In some embodiments, the hypotaurine or an analog or precursor thereof is not added to the cell culture medium incrementally over the course of a cell culture cycle.

Also provided herein are methods of producing a polypeptide of interest comprising the step of culturing a cell comprising a nucleic acid encoding the polypeptide in a cell culture medium, wherein the cell culture medium comprises one or more of components selected from the group consisting of (a) hypotaurine, (b) s-carboxymethylcysteine, (c) carnosine, (d) anserine, (e) butylated hydroxyanisole, (f) lipoic acid, and (g) quercitrin hydrate. In some embodiments, provided herein are methods of producing a polypeptide of interest comprising the step of culturing a cell comprising a nucleic acid encoding the polypeptide in a cell culture medium, wherein the cell culture medium comprises one or more of components selected from the group consisting of (a) hypotaurine, (b) s-carboxymethylcysteine, (c) carnosine, (d) anserine, (e) butylated hydroxyanisole, (f) lipoic acid, and (g) quercitrin hydrate, and wherein the cell culture medium comprising one or more of components (a)-(g) reduces the color intensity of a composition comprising the polypeptide produced by the cell as compared to a composition comprising the polypeptide produced by the cell cultured in a cell culture medium that does not comprise one or more of components (a)-(g). In some embodiments, the color intensity of the composition comprising the polypeptide is reduced by at least about 0.1%. In some embodiments, the color intensity of the composition comprising the polypeptide is reduced by at least about 5%. In some embodiments, the color intensity of the composition comprising the polypeptide is reduced by about 10% to about 30%. In some of the embodiments herein, the cell culture medium comprises one or more components in an amount selected from (a) hypotaurine at a concentration from about 2.0 mM to about 50.0 mM, (b) s-carboxymethylcysteine at a concentration from about 8.0 mM to about 12.0 mM, (c) carnosine at a concentration from about 8.0 mM to about 12.0 mM, (d) anserine at a concentration from about 3.0 mM to about 5.0 mM, (e) butylated hydroxyanisole at a concentration from about 0.025 mM to about 0.040 mM, (f) lipoic acid at a concentration from about 0.040 mM to about 0.060 mM, and (g) quercitrin hydrate at a concentration from about 0.010 mM to about 0.020 mM. In some of the embodiments herein, the one or more components selected from the group consisting of (a) hypotaurine, (b) s-carboxymethylcysteine, (c) carnosine, (d) anserine, (e) butylated hydroxyanisole, (f) lipoic acid; and (g) quercitrin hydrate is added to the cell culture medium on day 0 of a 14 day cell culture cycle.

In another aspect, provided herein are methods of producing a polypeptide of interest comprising the step of culturing a cell comprising a nucleic acid encoding the polypeptide in a cell culture medium. In some embodiments, provided herein are methods of producing a polypeptide of interest comprising the step of culturing a cell comprising a nucleic acid encoding the polypeptide in a cell culture medium, wherein the cell culture medium comprises hypotaurine or an analog or precursor thereof, and wherein the cell culture medium comprising the hypotaurine or an analog of precursor thereof, reduces the color intensity of a composition comprising the polypeptide produced by the cell as compared to the color intensity of a composition comprising the polypeptide produced by the cell cultured in a cell culture medium that does not comprise the hypotaurine or an analog or precursor thereof. In some embodiments, the color intensity of the composition comprising the polypeptide is reduced by at least about 0.1%. In some embodiments, the color intensity of the composition comprising the polypeptide is reduced by at least about 5%. In some embodiments, the color intensity of the composition comprising the polypeptide is reduced by about 10% to about 30%. In some embodiments herein, the cell culture medium comprises the hypotaurine or an analog or precursor thereof, at a concentration from at least about 0.0001 mM. In some embodiments herein, the cell culture medium comprises the hypotaurine or an analog or precursor thereof, at a concentration from about 0.5 mM to about 500 mM. In some embodiments, the cell culture medium comprises the hypotaurine or an analog or precursor thereof, at a concentration from about 1.0 mM to about 40 mM. In some embodiments herein, the hypotaurine or an analog or precursor thereof is selected from the group consisting of hypotaurine, s-carboxymethylcysteine, cysteamine, cysteinesulphinic acid, and taurine. In some of the embodiments herein, the hypotaurine or an analog or precursor thereof is added to the cell culture medium on day 0 of a 14 day cell culture cycle. In some embodiments, the hypotaurine or an analog or precursor thereof is not added to the cell culture medium incrementally over the course of a cell culture cycle.

In any of the embodiments herein, the cell culture medium used in the methods described herein can be a chemically defined cell culture medium of a chemically undefined cell culture medium. The cell culture medium provided herein can be used a basal cell culture medium or as a feed cell medium. In some embodiments, a cell culture medium provided herein is used in a method for culturing the cell during the cell's growth phase. In some embodiments, a cell culture medium provided herein is used in a method for culturing the cell during the cell's production phase. In any of the methods herein the cell may be a mammalian cell such as a CHO cell. In some embodiments, the polypeptide of interest is an antibody or fragment thereof.

In further embodiments herein the polypeptide of interest is recovered. A composition comprising the recovered polypeptide can be subjected to at least one purification step before assessment of color intensity using a quantitative or qualitative color assay as described herein. In some embodiments, the composition comprising the recovered polypeptide is a liquid composition or a non-liquid composition. In some embodiments, the liquid composition or non-liquid composition comprising a recovered polypeptide can be assessed for color intensity using a color assay as described herein or known in the art. For example, a non-liquid composition comprising the recovered polypeptide can be a lyophilized composition that is subsequently reconstituted before measurement of color intensity. In some embodiments herein, the color intensity of a composition comprising the polypeptide produced by the cell cultured in a cell culture medium provided herein is reduced by at least 0.1% as compared to the color intensity of a composition comprising the polypeptide produced by the cell cultured in a cell culture medium that does not comprise a media component as described herein (e.g., hypotaurine or an analog or precursor thereof). In some embodiments, the color intensity is reduced by at least about 0.1%, by at least about 0.2%, by at least about 0.3%, by at least about 0.4%, by at least about 0.5%, by at least about 0.6%, by at least about 0.7%, by at least about 0.8%, by at least about 0.8%, or by at least about 0.9% to about 1.0%. In some embodiments, the color intensity is reduced by at least about 1%, by at least about 2%, by at least about 3%, by at least about 4%, by at least about 5%, by at least about 10%, by at least about 15%, by at least about 20%, by at least about 25%, by at least about 30%, by at least about 35%, by at least about 40%, by at least about 45%, by at least about 50%, by at least about 60%, by at least about 70%, by at least about 80%, or by at least about 90% to about 100%. In some embodiments, the color intensity is reduced by about 0.1%, about 0.2%, about 0.3%, about 0.4%, about 0.5%, about 0.6%, about 0.7%, about 0.8%, about 0.9% to about 1.0%. In some embodiments, the color intensity is reduced by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 45%, about 50%, about 60%, about 70%, about 80%, about 90% to about 100%. In some embodiments, the color intensity is reduced by from about 1% to about 10%, from about 5% to about 15%, from about 5% to about 20%, from about 5% to about 25%, from about 5% to about 30%, from about 5% to about 35%, from about 5% to about 40%, from about 5% to about 45%, from about 5% to about 50%, from about 10% to about 20%, or from about 15% to about 25%. In some embodiments, a composition comprising a recovered polypeptide appears as a colorless or slightly colored liquid or composition. A liquid or composition can be determined to be colorless or slightly colored using a color assay as described herein or a color assay known to one of skill in the art. In a further embodiment, the composition is a pharmaceutical composition that optionally further comprises a pharmaceutically acceptable carrier as described herein.

Methods of administering a polypeptide as detailed herein are also provided. For example, a method is provided for administering to an individual a formulation comprising a polypeptide, wherein the formulation has the polypeptide at a concentration greater than at least about 100 mg/mL, at least about 125 mg/mL, or at least about 150 mg/mL and has a color intensity value greater than B3, B4, B5, B6, B7, B8, or B9 as measured by the COC assay. In some aspects, the color intensity value as determined by the COC assay can be any one of, but not limited to, B, BY, Y, GY, or R, wherein higher values indicate a lighter color intensity. Formulations comprising a polypeptide of interest may be suitable for injection, such as subcutaneous injection into an individual (e.g., subcutaneous injection into a human). In some aspects, a formulation comprising a polypeptide of interest suitable for injection (e.g., suitable for subcutaneous injection) is at a concentration greater than at least 100 mg/mL, at least 125 mg/mL, or at least 150 mg/mL and has a color intensity value greater than B3, B4, B5, B6, B7, B8, or B9 as measured by the COC assay. In some aspects, the color intensity value as determined by the COC assay can be any one of, but not limited to, B, BY, Y, GY, or R, wherein higher values indicate a lighter color intensity.

Other methods are provided throughout, such as in the Brief Summary of the Invention and elsewhere.

Polypeptide Production

The cell culture media detailed herein can be used in a method of culturing cells to produce polypeptides, including particular antibodies. The medium may be used in a method of culturing cells, whether by batch culture, fed batch culture or perfusion culture, and can be used in a method of producing any polypeptide including any aspects or embodiments of the polypeptide as described herein. The polypeptides produced by the compositions (e.g., a cell cultured in a cell culturing medium provided herein) and methods detailed herein and present in the compositions (e.g., cell culture media comprising the produced polypeptide) provided herein may be homologous to the host cell, or preferably, may be exogenous, meaning that they are heterologous, i.e., foreign, to the host cell being utilized, such as a human protein produced by a Chinese hamster ovary cell, or a yeast polypeptide produced by a mammalian cell. In one variation, the polypeptide is a mammalian polypeptide (such as an antibody) directly secreted into the medium by the host cell. In another variation, the polypeptide is released into the medium by lysis of a cell comprising a nucleic acid encoding the polypeptide.

Any polypeptide that is expressible in a host cell may be produced in accordance with the present disclosure and may be present in the compositions provided. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, etc.

Methods for producing polypeptides, such as antibodies, in cell culture are well known in the art. Provided herein are non-limiting exemplary methods for producing an antibody (e.g., full length antibodies, antibody fragments and multispecific antibodies) in cell culture. The methods herein can be adapted by one of skill in the art for the production of other proteins, such as protein-based inhibitors. See *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); *Short Protocols in Molecular Biology* (Ausubel et al., eds., J. Wiley and Sons, 2002); *Current Protocols in Protein Science*, (Horswill et al., 2006); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010) for generally well understood and commonly employed techniques and procedures for the production of proteins (e.g., therapeutic proteins), which are all incorporated herein by reference in their entirety.

(A) Antibody Preparation

The antibody produced in cell culture using a cell culture medium provided herein is directed against an antigen of interest. Preferably, the antigen is a biologically important polypeptide and administration of compositions comprising the antibody to a mammal suffering from a disorder can result in a therapeutic benefit in that mammal.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Monoclonal antibodies of interest can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4):265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of interest or a fragment thereof, and an adjuvant, such as monophosphoryl lipid A (MPL)/trehalose dicrynomycolate (TDM) (Ribi Immunochem. Research, Inc., Hamilton, Mont.). Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies. The binding specificity of monoclonal antibodies produced by hybridoma cells may be determined by immunoprecipitation or by an in vitro binding assay, such as radioimmunoassay (MA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In some embodiments, the hybridoma cells are cultured in a cell culture medium provided herein. In some embodiments, the hybridoma cells are cultured in a cell culture medium comprising one or more media components selected from the group consisting of hypotaurine, s-carboxymethylcysteine, anserine, butylated hydroxyanisole, carnosine, lipoic acid, and quercitrin hydrate. In some embodiments, the one or more media component is hypotaurine or an analog or precursor thereof. In some embodiments, the hypotaurine or an analog or precursor thereof is selected from the group consisting of hypotaurine, s-carboxymethylcysteine, cysteamine, cysteinesulphinic acid, and taurine.

Antibodies may be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(iii) Certain Library Screening Methods

Antibodies can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of interest can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$M).

Alternatively, the repertoires may be cloned sequentially into the same vector, e.g. as described in Barbas et al., *Proc.*

Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique 1: 11-15 (1989)) in the method of Hawkins et al., J. Mol. Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about $10^{-9}$ M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci USA, 88: 7978-7982 (1991), or by alkali, e.g. as described in Marks et al., J. Mol. Biol., 222: 581-597 (1991), or by antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of interest is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA,* 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of interest.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies of interest can be constructed by combining Fv clone variable domain sequence(s) selected from human-derived phage display libraries with known human constant domain sequence(s) as described above. Alternatively, human monoclonal antibodies of interest can be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al. *J. Immunol.* 147: 60 (1991).

(vii) Single-Domain Antibodies

In some embodiments, an antibody of interest is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(B) Vectors, Host Cells, and Recombinant Methods

Antibodies produced by a cell cultured in a cell culture medium provided herein may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

An antibody may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(ii) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ, plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

(iv) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Envinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frupperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, petunia, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TM cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in a cell culture medium provided herein modified as appropriate for inducing promoters, selecting transformants, or amplifying the genes encoding the desired sequences.

Cell Growth and Polypeptide Production

Generally the cells are combined (contacted) with any of the cell culture media described herein under one or more conditions that promote any of cell growth, maintenance and/or polypeptide production. Methods of culturing a cell and producing a polypeptide employ a culturing vessel (bioreactor) to contain the cell and cell culture medium. The culturing vessel can be composed of any material that is suitable for culturing cells, including glass, plastic or metal. Typically, the culturing vessel will be at least 1 liter and may be 10, 100, 250, 500, 1000, 2500, 5000, 8000, 10,000 liters or more. The culture conditions, such as temperature, pH, and the like, are those previously used with the host cell selected for expression, and will be apparent to the ordinarily skilled artisan. Culturing conditions that may be adjusted during the culturing process include but are not limited to pH and temperature.

A cell culture is generally maintained in the initial growth phase under conditions conducive to the survival, growth and viability (maintenance) of the cell culture. The precise conditions will vary depending on the cell type, the organism from which the cell was derived, and the nature and character of the expressed polypeptide.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be cultured during the initial growth phase for a greater or lesser amount of time. In one variation, the cells are cultured for a period of time sufficient to achieve a viable cell density that is a given percentage of the maximal viable cell density that the cells would eventually reach if allowed to grow undisturbed. For example, the cells may be cultured for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are cultured, and the intrinsic growth rate of the cells, the cells may be cultured for 0, 1, 2, 3, 4, 5, 6, 7, 8, 9, 10, 11, 12, 13, 14, 15, 16, 17, 18, 19, 20 or more days. In some cases, the cells may be allowed to grow for a month or more.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

An initial culturing step is a growth phase, wherein batch cell culture conditions are modified to enhance growth of recombinant cells, to produce a seed train. The growth phase generally refers to the period of exponential growth where cells are generally rapidly dividing, e.g. growing. During this phase, cells are cultured for a period of time, usually, but not limited to, 1 to 4 days, e.g. 1, 2, 3, or 4 days, and under such conditions that cell growth is optimal. The determination of the growth cycle for the host cell can be determined for the particular host cell by methods known to those skilled in the art.

In the growth phase, a basal culture medium provided herein and cells may be supplied to the culturing vessel in batch. The culture medium in one aspect contains less than about 5% or less than 1% or less than 0.1% serum and other animal-derived proteins. However, serum and animal-derived proteins can be used if desired. At a particular point in their growth, the cells may form an inoculum to inoculate a culture medium at the start of culturing in the production phase. Alternatively, the production phase may be continuous with the growth phase. The cell growth phase is generally followed by a polypeptide production phase.

During the polypeptide production phase, the cell culture may be maintained under a second set of culture conditions (as compared to the growth phase) conducive to the survival and viability of the cell culture and appropriate for expression of the desired polypeptide. For example, during the subsequent production phase, CHO cells express recombinant polypeptides and proteins well within a range of 25° C. to 38° C. Multiple discrete temperature shifts may be employed to increase cell density or viability or to increase expression of the recombinant polypeptide or protein. In one aspect, a medium as provided herein reduces the presence of metabolic by-products when used in a method of increasing polypeptide production as compared to contaminants obtained when the polypeptide is produced in a different medium. In one variation, the contaminants are reactive oxygen species. In one aspect, a medium as provided herein reduces color intensity of a polypeptide product when used in a method of increasing production of the polypeptide as compared to color intensity obtained when the polypeptide product is produced in a different media. In one variation, a method of increasing polypeptide production comprises a temperature shift step during the polypeptide production phase. In a further variation, a temperature shift step comprises a shift of the temperature from 31° C. to 38° C., from 32° C. to 38° C., from 33° C. to 38° C., from 34° C. to 38° C., from 35° C. to 38° C., from 36° C. to 38° C., from 31° C. to 32° C., from 31° C. to 33° C., from 31° C. to 34° C., from 31° C. to 35° C., or from 31° C. to 36° C.

The cells may be maintained in the subsequent production phase until a desired cell density or production titer is reached. In one embodiment, the cells are maintained in the subsequent production phase until the titer to the recombinant polypeptide reaches a maximum. In other embodiments, the culture may be harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture.

In certain cases, it may be beneficial or necessary to supplement the cell culture during the subsequent production phase with nutrients or other medium components that have been depleted or metabolized by the cells. For example, it might be advantageous to supplement the cell culture with nutrients or other medium components observed to have been depleted during monitoring of the cell culture. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

A component provided herein (e.g., hypotaurine an analog or precursor thereof) can be added to the cell culture medium at any time during the cell culture cycle. For example, hypotaurine may be added at any one or more of days 0-14 for a 14 day cell culture cycle (e.g., at any one or more of days 0, 1, 2, 3, 4, 5, 6, 7, 8, 9, 10, 11, 12, 13, or 14) at any amount to provide a cell culture medium comprising hypotaurine at a concentration provided herein (e.g., at least 0.0001 mM). It is therefore appreciated that for a 14 day cell culture cycle, hypotaurine may be added at any one or more of days 0-14 (e.g., at any one or more of days 0, 1, 2, 3, 4, 5, 6, 7, 8, 9, 10, 11, 12, 13 or 14) in any amount. As used herein "day 0" can refer to a cell culture medium that has been supplemented with a component provided herein (e.g., hypotaurine) before the cell culture medium has been applied to the cell culture. It is understood that a cell culture cycle can be any amount of days as long as the cells remain viable and/or sufficient levels of polypeptide are produced as can be determined by one of skill in the art. For example, a cell culture cycle can be at least 3 days, 4 days, 5 days, 6 days, at 7 days, 8 days, 9 days, 10 days, 11 days, 12 days, 13 days, 14 days, 15 days, 16 days, 17 days, 18 days, 19 days, or 20 days in duration. In some embodiments, a component provided herein (e.g., hypotaurine or an analog or precursor thereof) is added to the cell culture medium on at least on day of a cell culture cycle.

Polypeptide Purification

The polypeptide of interest preferably is recovered from the culture medium as a secreted polypeptide, although it also may be recovered from host cell lysates when directly expressed without a secretory signal. In one aspect, the polypeptide produced is an antibody, such as a monoclonal antibody.

The culture medium or lysate may be centrifuged to remove particulate cell debris. The polypeptide thereafter may be purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the polypeptide of interest may require modification to account for changes in the character of the polypeptide upon expression in recombinant cell culture. Polypeptides can be generally purified using chromatographic techniques (e.g., protein A, affinity chromatography with a low pH elution step and ion exchange chromatography to remove process impurities). For antibodies, the suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). Purified proteins may concentrated to provide a concentrated protein drug product as described herein, e.g., one with a protein concentration of at least 1 mg/mL or 10 mg/mL or 50 mg/mL or 75 mg/mL or 100 mg/mL or 125 mg/mL or 150 mg/mL or a concentration of about 1 mg/mL or 10 mg/mL or 50 mg/mL or 75 mg/mL or 100 mg/mL or 125 mg/mL or 150 mg/mL. It is understood that concentrated polypeptide products may be concentrated up to levels that are permissible under the concentration conditions, e.g., up to a concentration at which the polypeptide is no longer soluble in solution. For example, a polypeptide purification process can comprise the steps of harvesting cell culture fluid from polypeptide-producing cells and purifying the polypeptide through protein A affinity chromatography with further purification through anion and cation exchange chromatography, filtration for removal of virus, and a final ultrafiltration and diafiltration step for final formulation and concentration of the polypeptide. Non-limiting examples of methods for producing and purifying polypeptides for drug formulations are described in Kelley, B. *MAbs.,* 2009, 1(5): 443-452, which is incorporated herein in its entirety by reference.

Polypeptide Color Assessment

The polypeptides produced by the methods detailed herein and present in the compositions provided may be assessed for color at any step of the protein purification process. A method for assessing color may involve harvesting the cell culture fluid from cells cultured in the media detailed herein, purifying the polypeptide from cell culture fluid to obtain a composition (e.g., a solution) comprising the polypeptide and assessing the solution comprising the polypeptide for color. In one variation, a composition comprising the polypeptide is assessed for color after purification with Protein A affinity chromatography. In a further variation, a composition comprising the polypeptide is assessed for color after purification by ion exchange chromatography. In another variation, a composition comprising the polypeptide is assessed for color after purification by high performance liquid chromatography. In yet another variation, a composition comprising the polypeptide is assessed for color after purification by hydrophobic interaction chromatography. In still another variation, a composition comprising the polypeptide is assessed for color after purification by size exclusion chromatography. In one variation, a composition comprising the polypeptide is assessed for color after purification by filtration including microfiltration or ultrafiltration. In one variation, the composition comprising the polypeptide is concentrated prior to assessing for color (e.g., the composition may comprise at least 1 mg/mL, 10 mg/mL, 50 mg/mL, 75 mg/mL, 100 mg/mL, 125 mg/mL or 150 mg/mL polypeptide, such as an antibody). The composition comprising the polypeptide can be concentrated by centrifugation, filter devices, semi-permeable membranes, dialysis, precipitation, ion exchange chromatography, affinity chromatography, high performance liquid chromatography, or hydrophobic interaction chromatography. In one variation, the polypeptide can be concentrated by lyophilization and resuspended prior to assessment for color. The composition comprising the polypeptide may be assessed for color after purification with one or more of the techniques detailed herein. Color assessment of the composition comprising the polypeptide after the composition has undergone one or more freeze thaw cycle(s) is contemplated herein. Methods for color assessment of cell culture fluid containing the polypeptide prior to purification or concentration of the polypeptide is further contemplated herein.

The polypeptides produced by the methods detailed herein with the media described herein (or present in the compositions provided) may be assessed for color by use of one or more visual color standards. Methods for color assessment of composition comprising the polypeptide include use of an international or national color standard such as, but not limited to, the United States Pharmacopoeia color standard and the European Pharmacopoeia color standard. See USP-24 Monograph 631 Color and Achromaticity. *United States Pharmacopoeia Inc.,* 2000, p. 1926-1927 and Council of Europe. *European Pharmacopoeia,* 2008, 7*th* Ed. P.22, which are incorporated herein by reference in their entirety. For example, the Color, Opalescence and Coloration (COC) assay may be used to assess color of a solution containing the polypeptide. In one variation, identical tube of colorless, transparent, neutral glass of 12 mm external diameter are used to compare 2.0 mL of the composition comprising the polypeptide with 2.0 mL of water or of the solvent or of the reference solution prescribed in the monograph. The colors are compared in diffused daylight and viewed horizontally against a white background for color determination, measurement, or assessment. In another variation, identical tubes of colorless, transparent, neutral glass with a flat base and an internal diameter of 15 mm to 25 mm are used to compare the composition comprising the polypeptide with water or the solvent or the reference solution prescribed in the monograph, the depth of the layer being 40 mm. The colors are compared in diffused daylight and viewed vertically against a white background for color determination, measurement, or assessment. In one variation, color determination, measurement or assessment can be done by human visual inspection. In another variation, color determination, measurement, or assessment can be done by using an automated process. For example, the tubes can be loaded in a machine that images the tubes for processing of the images with an algorithm to determine, measure, or assess the color. It is understood that the reference standards for the COC assay can be any one of, but not limited to, brown (B), brownish-yellow (BY), yellow (Y), greenish-yellow (GY), or red (R). Compositions comprising the polypeptide that are compared to the brown reference standard can be given a brown reference standard value of B1 (darkest), B2, B3, B4, B5, B6, B7, B8, or B9 (lightest). Compositions comprising the polypeptide that are compared to the brownish-yellow reference standard can be given a brownish-yellow reference standard value of BY1 (darkest), BY2, BY3, BY4, BY5, BY6, or BY7 (lightest). Compositions comprising the polypeptide that are compared to the yellow reference standard can be given a yellow reference standard value of Y1 (darkest), Y2, Y3, Y4, Y5, Y6, or Y7 (lightest). Compositions comprising the polypeptide that are compared to the greenish-yellow reference standard can be given a greenish-yellow reference standard value of GY1 (darkest), GY2, GY3, GY4, GY5, GY6, or GY7 (lightest). Compositions comprising the polypeptide that are compared to the red reference standard can be given a red reference standard value of R1 (darkest), R2, R3, R4, R5, R6, or R7 (lightest). In one aspect, an acceptable color is any color except that which measures darkest on a scale provided herein (e.g., except R1 for a red reference standard value). In one variation, the color of the composition comprising the polypeptide produced by cells cultured in the media detailed herein has a reference standard value as described in Table 3. As is described herein, it is understood that in one aspect the media that may be used in the methods and compositions herein result in a polypeptide composition (which in one variation is a composition comprising at least 100 mg/mL or 125 mg/mL or 150 mg/ml polypeptide) having a reference standard color value selected from the group consisting of B3, B4, B5, B6, B7, B8, B9, BY3, BY4, BY5, BY6, BY7, Y3, Y4, Y5, Y6, Y7, GY3, GY4, GY5, GY6, GY7, R3, R4, R5, R6 and R7. In one aspect, the media that may be used in the methods and compositions herein result in a polypeptide composition (which in one variation is a composition comprising at least 100 mg/mL or 125 mg/mL or 150 mg/ml polypeptide) having a reference standard color value of greater than any one of B4, B5, B6, B7, B8, BY4, BY5, BY6, Y4, Y5, Y6, GY4, GY5, GY6, GY7, R3, R4, R5 and R6. As would be understood to the skilled artisan, descriptions of reference standard color values are applicable to, and may further modify descriptions of, any of the media, methods or compositions detailed herein.

TABLE 3

Exemplary reference standard values

| Reference standard | Reference standard value |
|---|---|
| (a) Brown | from about B1 to about B9; from about B1 to about B8; from about B1 to about B7; from about B1 to about B6; from about B1 to about B5; from about B1 to about B4; from about B1 to about B3; from about B1 to about B2; from about B2 to about B9; from about B3 to about B9; from about B4 to about B9; from about B5 to about B9; from about B6 to about B9; from about B7 to about B9; from about B8 to about B9; from about B2 to about B8; from about B3 to about B7; from about B4 to about B6; from about B5 to about B7; from about B6 to about B8; about any of B1 or B2 or B3 or B4 or B5 or B6 or B7 or B8 or B9; at least about any of B1 or B2 or B3 or B4 or B5 or B6 or B7 or B8 or B9. Preferably B3 to B9. Most preferably B4 to B9. |
| (b) Brownish-Yellow | from about BY1 to about BY7; from about BY1 to about BY6; from about BY1 to about BY5; from about BY1 to about BY4; from about BY1 to about BY3; from about BY1 to about BY2; from about BY2 to about BY7; from about BY3 to about BY7; from about BY4 to about BY7; from about BY5 to about BY7; from about BY6 to about BY7; from about BY2 to about BY6; from about BY3 to about BY5; from about BY4 to about BY6; from about BY5 to about BY6; about any of BY1 or BY2 or BY3 or BY4 or BY5 or BY6 or BY7; at least about |

TABLE 3-continued

Exemplary reference standard values

| Reference standard | Reference standard value |
| --- | --- |
| | any of BY1 or BY2 or BY3 or BY4 or BY5 or BY6 or BY7. Preferably BY3 to BY7. Most preferably BY4 to BY7. |
| (c) Yellow | from about Y1 to about Y7; from about Y1 to about Y6; from about Y1 to about Y5; from about Y1 to about Y4; from about Y1 to about Y3; from about Y1 to about Y2; from about Y2 to about Y7; from about Y3 to about Y7; from about Y4 to about Y7; from about Y5 to about Y7; from about Y6 to about Y7; from about Y2 to about Y6; from about Y3 to about Y5; from about Y4 to about Y6; from about Y5 to about Y6; about any of Y1 or Y2 or Y3 or Y4 or Y5 or Y6 or Y7; at least about any of Y1 or Y2 or Y3 or Y4 or Y5 or Y6 or Y7. Preferably Y3 to Y7. Most preferably Y4 to Y7. |
| (d) Greenish-Yellow | from about GY1 to about GY7; from about GY1 to about GY6; from about GY1 to about GY5; from about GY1 to about GY4; from about GY1 to about GY3; from about GY1 to about GY2; from about GY2 to about GY7; from about GY3 to about GY7; from about GY4 to about GY7; from about GY5 to about GY7; from about GY6 to about GY7; from about GY2 to about GY6; from about GY3 to about GY5; from about GY4 to about GY6; from about GY5 to about GY6; about any of GY1 or GY2 or GY3 or GY4 or GY5 or GY6 or GY7; at least about any of GY1 or GY2 or GY3 or GY4 or GY5 or GY6 or GY7. Preferably GY3 to GY7. Most preferably GY4 to GY7. |
| (e) Red | from about R1 to about R7; from about R1 to about R6; from about R1 to about R5; from about R1 to about R4; from about R1 to about R3; from about R1 to about R2; from about R2 to about R7; from about R3 to about R7; from about R4 to about R7; from about R5 to about R7; from about R6 to about R7; from about R2 to about R6; from about R3 to about R5; from about R4 to about R6; from about R5 to about R6; about any of R1 or R2 or R3 or R4 or R5 or R6 or R7; at least about any of R1 or R2 or R3 or R4 or R5 or R6 or R7. Preferably R3 to R7. Most preferably R4 to R7. |

In another example, the polypeptides produced by the methods detailed herein with the media described herein (or present in the compositions provided) may be assessed for color with a quantitative assay. In some embodiments, the quantitative assay can be done using an automated process. In some embodiments, a higher value (e.g., higher numerical value) provided by the quantitative assay indicates a higher color intensity and a lower value (e.g., lower numerical value) indicates a lower color intensity.

A color assay detailed herein may find use in assessing color of any solution (e.g., a polypeptide-containing solution), including, but not limited to, the polypeptide compositions provided herein.

IV. Compositions and Pharmaceutical Formulations

Compositions comprising the cell culture medium and one or more other component, such as a cell or a desired polypeptide (e.g., an antibody), are also provided. A cell comprising a nucleic acid encoding a polypeptide of interest (e.g., an antibody) can secrete the polypeptide into a cell culture medium of the invention during cell culture. Accordingly, compositions of the invention can comprise a cell that produces the polypeptide and a cell culture medium provided herein that the polypeptide is secreted into. Compositions comprising the produced polypeptide and a cell culture medium provided herein are also contemplated. In some aspects of the invention, a composition comprises (a) a cell comprising a nucleic acid encoding a polypeptide; and (b) a cell culture medium are provided herein. In some aspects, the composition comprises (a) a polypeptide; and (b) a cell culture medium as provided herein, wherein the polypeptide is secreted into the medium by a cell comprising an isolated nucleic acid encoding the polypeptide. In other aspects, the composition comprises: (a) a polypeptide; and (b) a cell culture medium as provided herein, wherein the polypeptide is released into the medium by lysis of a cell comprising an isolated nucleic acid encoding the polypeptide. The cell of the composition may be any cell detailed herein (e.g., a CHO cell) and the medium of the composition may be any medium detailed herein, such as a medium comprising one or more compounds as detailed in Table 1 or Table 2. Likewise, the polypeptide of the composition may be any polypeptide detailed herein, such as an antibody. In some aspects, the composition may have a color. In some embodiments, the color is determined, measured, or assessed by use of one or more visual color standards. The visual color standard can be an international or national color standard such as, but not limited to, the United States Pharmacopoeia color standard and the European Pharmacopoeia color standard. See USP-24 Monograph 631 Color and Achromaticity. *United States Pharmacopoeia Inc.*, 2000, p. 1926-1927 and Council of Europe. *European Pharmacopoeia*, 2008, 7$^{th}$ Ed. P.22. Accordingly, in some embodiments, a composition comprising (a) a polypeptide; and (b) a cell culture medium provided herein is assessed for color intensity. In a further embodiment, the polypeptide is isolated and/or purified before assessment of color intensity. In some embodiments, a color intensity of a composition comprising (a) a polypeptide; and (b) a cell culture medium provided herein is used to predict the color intensity of the final protein composition. For example, a composition comprising a polypeptide and a cell culture medium provided herein is measured for color intensity using the COC assay as described herein. If the color intensity value is greater than B3, B4, B5, B6, B7, B8, or B9 then there is an increased likelihood that the final protein composition will have a color intensity value of greater than B3, B4, B5, B6, B7, B8, or B9. In some embodiments, the composition comprising a polypeptide and the cell culture medium is subjected to at least one purification step before measurement of color intensity. In some embodiments, the final protein composition is a pharmaceutical formulation. In some aspects, a composition as provided herein comprises a polypeptide at a concentration of at least about 1 mg/mL, 10 mg/mL or 25 mg/mL or 50 mg/mL or 75 mg/mL to about 100 mg/mL or at a concentration of about 1 mg/mL, 10 mg/mL or 25 mg/mL or 50 mg/mL or 75 mg/mL to about 100 mg/mL. In some aspects, a composition as provided herein comprises a polypeptide at a concentration of at least 100 mg/mL or 125 mg/mL or 150 mg/mL or at a concentration of about 100 mg/mL or 125 mg/mL or 150 mg/mL or 175 mg/mL or 200 mg/mL.

Compositions (e.g., pharmaceutical formulations) of the polypeptides (e.g. a therapeutic polypeptide) produced by any of the methods described herein are prepared by mixing a polypeptide having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers, antioxidants, preservatives, low molecular weight (less than about 10 residues) polypeptides, proteins; hydrophilic polymers; amino acids; monosaccharides, disaccharides, and other carbohydrates, chelating agents, sugars, salt-forming counter-ions, metal complexes (e.g. Zn-protein complexes), and/or non-ionic surfactants. Exemplary lyophilized polypeptide formulations are described in U.S. Pat. No. 6,267,958. Aqueous polypeptide formulations include those described in U.S. Pat. No. 6,171,586 and WO2006/044908, the latter formulations including a histidine-acetate buffer. In some embodiments, the pharmaceutical formulation is administered to a mammal such as a human. Pharmaceutical formulations of the polypeptide (e.g., an antibody) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Accordingly, polypeptide-containing formulations as provided herein may be suitable for injection, such as subcutaneous injection into an individual (e.g., subcutaneous injection into a human). The pharmaceutical formulations to be used for in vivo administration are generally sterile. Sterility may be readily accomplished, for example by filtration through sterile filtration membranes.

In some aspects, a composition (e.g., pharmaceutical formulation) as provided herein comprises a polypeptide (e.g., a therapeutic polypeptide) at a concentration of at least about 1 mg/mL, 10 mg/mL, 25 mg/mL, 50 mg/mL, or 75 mg/mL, or at a concentration of about 1 mg/mL, about 10 mg/mL, about 25 mg/mL, about 50 mg/mL, or about 75 mg/mL up to about 100 mg/mL. In other aspects, a composition (e.g., pharmaceutical formulation) as provided herein comprises a polypeptide (e.g., a therapeutic polypeptide) at a concentration of at least about 100 mg/mL, 125 mg/mL, 150 mg/mL, 200 mg/mL, or 250 mg/mL, or at a concentration of about 100 mg/mL, about 125 mg/mL, about 150 mg/mL, about 175 mg/mL, about 200 mg/mL, or about 250 mg/mL. In some embodiments, a pharmaceutical formulation as provided herein comprises a polypeptide at a concentration greater than at least about 1 mg/mL, at least about 10 mg/mL, at least about 25 mg/mL, at least about 50 mg/mL, or at least about 75 mg/mL and has a color intensity value greater than B3, B4, B5, B6, B7, B8, or B9 as measured by the COC assay. In some embodiments, a pharmaceutical formulation as provided herein comprises a polypeptide at a concentration greater than at least about 100 mg/mL, at least about 125 mg/mL, at least about 150 mg/mL, or at least about 200 mg/mL and has a color intensity value greater than B3, B4, B5, B6, B7, B8, or B9 as measured by the COC assay. In some aspects, the color intensity value as determined by the COC assay can be any one of, but not limited to, B, BY, Y, GY, or R, wherein higher values indicate a lighter color intensity. In some aspects, a pharmaceutical formulation as provided herein comprises a polypeptide at a concentration greater than at least about 1 mg/mL, at least about 10 mg/mL, at least about 25 mg/mL, at least about 50 mg/mL, or at least about 75 mg/mL and has a color intensity value less than a color intensity value of a reference solution as measured by a color assay. In some aspects, a pharmaceutical formulation as provided herein comprises a polypeptide at a concentration greater than at least about 100 mg/mL, at least about 125 mg/mL, at least about 150 mg/mL, or at least about 200 mg/mL and has a color intensity value less than a color intensity value of a reference solution as measured by a color assay. For example, the color intensity of a composition (e.g., pharmaceutical formulation) comprising a polypeptide (e.g., a therapeutic polypeptide) can be reduced by at least 0.1% or by about 5% to about 50% as compared to a composition comprising the polypeptide produced by a cell cultured in a cell culture medium that does not comprise the one or more of components of Table 1 or Table 2.

V. Articles of Manufacture or Kits

A kit for supplementing a cell culture medium with chemically defined constituents is described. The kit may contain dried constituents to be reconstituted, and may also contain instructions for use (e.g., for use in supplementing a medium with the kit constituents). The kit may contain the constituents provided herein in amounts suitable to supplement a cell culture medium. In some aspects, the kit contains one or more constituent selected from the group consisting of hypotaurine, s-carboxymethylcysteine, anserine, butylated hydroxyanisole, carnosine, lipoic acid, and quercitrin hydrate in amounts to supplement a cell culture medium with a constituent concentration as provided in Table 1 or Table 2. In some embodiments, a kit comprises one or more of: (a) hypotaurine in an amount to provide from about 2.0 mM to about 50.0 mM hypotaurine in the cell culture medium; (b) s-carboxymethylcysteine in an amount to provide from about 8.0 mM to about 12.0 mM s-carboxymethylcysteine in the cell culture medium; (c) carnosine in an amount to provide from about 8.0 mM to about 12.0 mM carnosine in the cell culture medium; (d) anserine in an amount to provide from about 3.0 mM to about 5.0 mM anserine in the cell culture medium; (e) butylated hydroxyanisole in an amount to provide from about 0.025 mM to about 0.040 mM butylated hydroxyanisole; (f) lipoic acid in an amount to provide from about 0.040 mM to about 0.060 mM lipoic acid in the cell culture medium; and (g) quercitrin hydrate in an amount to provide from about 0.010 mM to about 0.020 mM quercitrin hydrate in the cell culture medium. In some aspects, the kit contains one or more constituent, wherein the one or more constituent is hypotaurine or an analog or precursor thereof. In some embodiments, the hypotaurine or an analog or precursor thereof is selected from the group consisting of hypotaurine, s-carboxymethylcysteine, cysteamine, cysteinesulphinic acid, and taurine. In some embodiments, a kit for supplementing a cell culture medium with chemically defined constituents, the kit comprising hypotaurine or an analog or precursor thereof at a concentration of at least about 0.0001 mM, and wherein the hypotaurine or an analog or precursor is selected from the group consisting of hypotaurine, s-carboxymethylcysteine, cysteamine, cysteinesulphinic acid, and taurine.

In another aspect of the invention, an article of manufacture is provided comprising a container which holds the cell culture medium of the invention and optionally provides instructions for its use. Suitable containers include, for example, bottles and bags. The container may be formed from a variety of materials such as glass or plastic. The container holds the cell culture medium and the label on, or associated with, the container may indicate directions for use (e.g., for use in culturing cells). The article of manufacture may further include other materials desirable from a commercial and user standpoint, including other buffers, diluents and package inserts with instructions for use.

The following Examples are provided to illustrate but not to limit the invention.

EXAMPLES

Media have been identified that produce a protein product (e.g., a protein drug product) with acceptable quality attributes, such as reduced color intensity, particularly when the protein product is present as a concentrated solution (e.g., to a concentration of at least about 1 mg/mL or at least about 100 mg/mL). Methods of culturing cells in the media provided herein are described, as are methods of producing a polypeptide using the media. A media may in one aspect comprise hypotaurine. In some of the aspects provided herein, the media comprises one or more hypotaurine analog or precursor thereof, such as carboxymethylcysteine. Each of the media constituents may be present in any value provided throughout. The media may be chemically defined or chemically undefined. The media may reduce the presence of reactive oxygen species when used in a method of polypeptide production as compared to the polypeptide produced in different media. The media finds use through all phases of cell culture and polypeptide production and may be used in the basal and/or feed medium. A polypeptide produced by any of the methods described herein is provided, as is a pharmaceutical composition comprising a polypeptide produced as detailed herein. In one aspect, the pharmaceutical compositions comprise the polypeptide at a concentration of at least or about any of 100 mg/mL, 125 mg/mL, or 150 mg/mL. Methods of making and compositions comprising antibodies are particularly contemplated. Kits for supplementing a cell culture medium with chemically defined constituents are also described.

Example 1: Identification of Antioxidant Compounds Capable of Reducing Color in Antibody Compositions Compounds that have been reported to react with an oxidant were screened for their ability to reduce the color of protein containing compositions (Table 4). For antioxidant screening, a total volume of 40 ml media was prepared by mixing 1 part basal Media 1 and 0.3 part feed Media 2 to mirror a representative ratio of media used in cell culture conditions (Table 5). The mixture of Media 1 and Media 2, which was previously shown to increase the color intensity of antibody-containing solutions when used for culturing antibody-producing cells, was supplemented with one of 30 antioxidant compounds and spiked with 2 g/L IgG1 monoclonal antibody. The samples were incubated at 37° C. with shaking at 250 rpm for a five day incubation period. Two control samples were included in the screening assay: 1) a 40 ml sample of a Media 1 and Media 2 mixture containing 2 g/L IgG1 monoclonal antibody that was incubated for 5 days at 37° C. with shaking at 250 rpm without antioxidant (positive control), and 2) a 40 mL sample of a media mixture prepared by mixing 1 part basal Media 3 and 0.3 part feed Media 4 (Table 5), which was previously shown to reduce the color intensity of antibody-containing solutions when used for culturing antibody-producing cells, spiked with 2 g/L IgG1 monoclonal antibody and incubated for 5 days at 37° C. with shaking at 250 rpm without antioxidant (negative control).

TABLE 4

Representative compounds screened for reduction of color

| Antioxidant | IUPAC | CAS # | 1X Test Concentration |
|---|---|---|---|
| 2,3-tert-butyl-4-hydroxyanisole | 2-tert-butyl-4-methoxyphenol | 25013-16-5 | 34.68 µM |
| 2,6-di-tert-butyl-4-methylphenol | 2,6-di-tert-butyl-4-methylphenol | 97123-41-6 | 102.11 µM |
| 3-aminopropane-1-sulfonic acid | 3-aminopropane-1-sulfonic acid | 3687-18-1 | 9.16 mM |
| Adenosylhomocysteine | S-(5'-Deoxyadenos-5'-yl)-L-homocysteine | 979-92-0 | 10.41 µM |
| Anserine | (2S)-2-(3-aminopropanamido)-3-(1-methyl-1H-imidazol-5-yl)propanoic acid; nitric acid | 10030-52-1 | 4.12 mM |
| B-Alanine | 3-aminopropanoic acid | 107-95-9 | 9.16 mM |
| B-carotene | 1,3,3-trimethyl-2-[(1E,3E,5E,7E,9E,11E,13E,15E,17E)-3,7,12,16-tetramethyl-18-(2,6,6-trimethylcyclohex-1-en-1-yl)octadeca-1,3,5,7,9,11,13,15,17-nonaen-1-yl]cyclohex-1-ene | 7235-40-7 | 9.31 µM |
| Butylated hydroxyanisole | 2-tert-butyl-4-methoxyphenol | 25013-16-5 | 31.62 µM |
| Butylated hydroxytoluene | 2,6-di-tert-butyl-4-methylphenol | 128-37-0 | 124.80 µM |

TABLE 4-continued

Representative compounds screened for reduction of color

| Antioxidant | IUPAC | CAS # | 1X Test Concentration |
|---|---|---|---|
| Carnosine | (2S)-2-(3-aminopropanamido)-3-(1H-imidazol-5-yl)propanoic acid | 305-84-0 | 10.00 mM |
| Carvedilol | [3-(9H-carbazol-4-yloxy)-2-hydroxypropyl][2-(2-methoxyphenoxy)ethyl]amine | 72956-09-3 | 21.53 μM |
| Curcumin | (1E,4Z,6E)-5-hydroxy-1,7-bis(4-hydroxy-3-methoxyphenyl)hepta-1,4,6-trien-3-one | 458-37-7 | 49.95 μM |
| Cysteamine | 2-aminoethane-1-thiol | 60-23-1 | 12.00 mM |
| Cysteamine hydrochloride | hydrogen 2-aminoethane-1-thiol chloride | 156-57-0 | 10.00 mM |
| Dexamethasone | (1R,2S,10S,11S,13R,14R,15S,17S)-1-fluoro-14,17-dihydroxy-14-(2-hydroxyacetyl)-2,13,15-trimethyltetracyclo[8.7.0.0^{2,7}.0^{11,15}]heptadeca-3,6-dien-5-one | 50-02-2 | 9.56 μM |
| Diallyldisulfide | 3-(prop-2-en-1-ylsulfanyl)prop-1-ene | 592-88-1 | 1.00 mM |
| DL-Lanthionine | 2-amino-3-[(2-amino-2-carboxyethyl)sulfanyl]propanoic acid | 3183-08-2 | 97.96 μM |
| DL-Thiorphan | 2-(2-benzyl-3-sulfanylpropanamido)acetic acid | 76721-89-6 | 0.10 mM |
| Ethoxyquin | 6-ethoxy-2,2,4-trimethyl-1,2-dihydroquinoline | 91-53-2 | 49.99 μM |
| Gallic acid | 3,4,5-trihydroxybenzoic acid | 149-91-7 | 14.11 μM |
| Gentisic acid sodium salt hydrate | sodium 2,5-dihydroxybenzoate | 4955-90-2 | 2.84 mM |
| Glutathione | 2-amino-4-({1-[(carboxymethyl)carbamoyl]-2-sulfanylethyl}carbamoyl)butanoic acid | 70-18-8 | 2.0 mM |
| Glutathione disulfide | 2-amino-4-[(2-{[2-(4-amino-4-carboxybutanamido)-2-[(carboxymethyl)carbamoyl]ethyl]disulfanyl}-1-[(carboxymethyl)carbamoyl]ethyl]carbamoyl]butanoic acid | 27025-41-8 | 2.0 mM |
| Glutathione reduced ethyl ester | (2S)-2-amino-4-{[(1R)-1-[(carboxymethyl)carbamoyl]-2-sulfanylbutyl]carbamoyl}butanoic acid | 92614-59-0 | 0.93 mM |
| Glycine | 2-aminoacetic acid | 56-40-6 | 13.32 mM |
| Hydrocortisone | (1S,2R,10S,11S,14R,15S,17S)-14,17-dihydroxy-14-(2-hydroxyacetyl)-2,15-dimethyltetracyclo[8.7.0.0^{2,7}.0^{11,15}]heptadec-6-en-5-one | 50-23-7 | 55.03 mM |
| Hypotaurine | 2-aminoethane-1-sulfinate | 300-84-5 | 9.16 mM |
| Isethionic acid ammonium salt | ammonium 2-hydroxyethane-1-sulfonate | 57267-78-4 | 9.16 mM |
| L-Cysteine-glutathione Disulfide | (2S)-2-amino-4-{[(1R)-2-{[(2R)-2-amino-3,3-dihydroxypropyl]sulfanyl}-1-[(carboxymethyl)carbamoyl]-2-sulfanylideneethyl]carbamoyl}butanoic acid | 13081-14-6 | 0.73 mM |
| L-Cysteinesulfinic acid monohydrate | (2R)-2-amino-3-[(R)-sulfino]propanoic acid hydrate | 207121-48-0 | 9.15 mM |
| Lipoic Acid | 5-[(3R)-1,2-dithiolan-3-yl]pentanoic acid | 1200-22-2 | 50.40 μM |
| Lipoic acid reduced | 6,8-disulfanyloctanoic acid | 462-20-4 | 48.00 μM |
| Mercaptopropionyl glycine | 2-(2-sulfanylpropanamido)acetic acid | 1953-02-2 | 10.00 mM |
| Methionine | 2-amino-4-(methylsulfanyl)butanoic acid | 59-51-8 | 5.00 mM |
| Methylenebis(3-thiopropionic acid) | 3-({[(2-carboxyethyl)sulfanyl]methyl}sulfanyl)propanoic acid | 4265-57-0 | 0.99 mM |
| Oxalic acid | oxalic acid | 144-62-7 | 500.94 μM |
| Quercetrin hydrate | 2-(3,4-dihydroxyphenyl)-5,7-dihydroxy-3-{[(2S,3R,4R,5R,6S)-3,4,5-trihydroxy-6-methyloxan-2-yl]oxy}-4H-chromen-4-one | 522-12-3 | 13.94 μM |
| Resveratrol | 5-[(E)-2-(4-hydroxyphenyl)ethenyl]benzene-1,3-diol | 501-36-0 | 98.58 μM |
| Retinoic acid | (2E,4E,6E,8E)-3,7-dimethyl-9-(2,6,6-trimethylcyclohex-1-en-1-yl)nona-2,4,6,8-tetraenoic acid | 302-79-4 | 2.0 μM |
| S-Carboxymethyl-L-cysteine | (2R)-2-amino-3-[(carboxymethyl)sulfanyl]propanoic acid | 638-23-3 | 10.00 mM |
| Selenium | selanylidene | 7782-49-2 | 1.40 μM |
| Selenomethionine | (2S)-2-amino-4-(methylselanyl)butanoic acid | 3211-76-5 | 30.09 μM |
| Silver diethyldithiocarbamate | silver(1+) ion (diethylcarbamothioyl)sulfanide | 1470-61-7 | 0.10 mM |
| Taurine | 2-aminoethane-1-sulfonic acid | 107-35-7 | 5.00 mM |
| Thiolactic acid | 2-sulfanylpropanoic acid amine | 79-42-5 | 10.00 mM |
| Tricine | 2-{[1,3-dihydroxy-2-(hydroxymethyl)propan-2-yl]amino}acetic acid | 5704-04-1 | 4.46 mM |
| Vitamin C | 2-(1,2-dihydroxyethyl)-4,5-dihydroxy-2,3-dihydrofuran-3-one | 50-81-7 | 9.82 μM |
| Vitamin E | (2R)-2,5,7,8-tetramethyl-2-[(4R,8R)-4,8,12-trimethyltridecyl]-3,4-dihydro-2H-1-benzopyran-6-ol | 10191-41-0 | 27.86 μM |

1X test concentration indicates final concentration in the media

Figure 2:
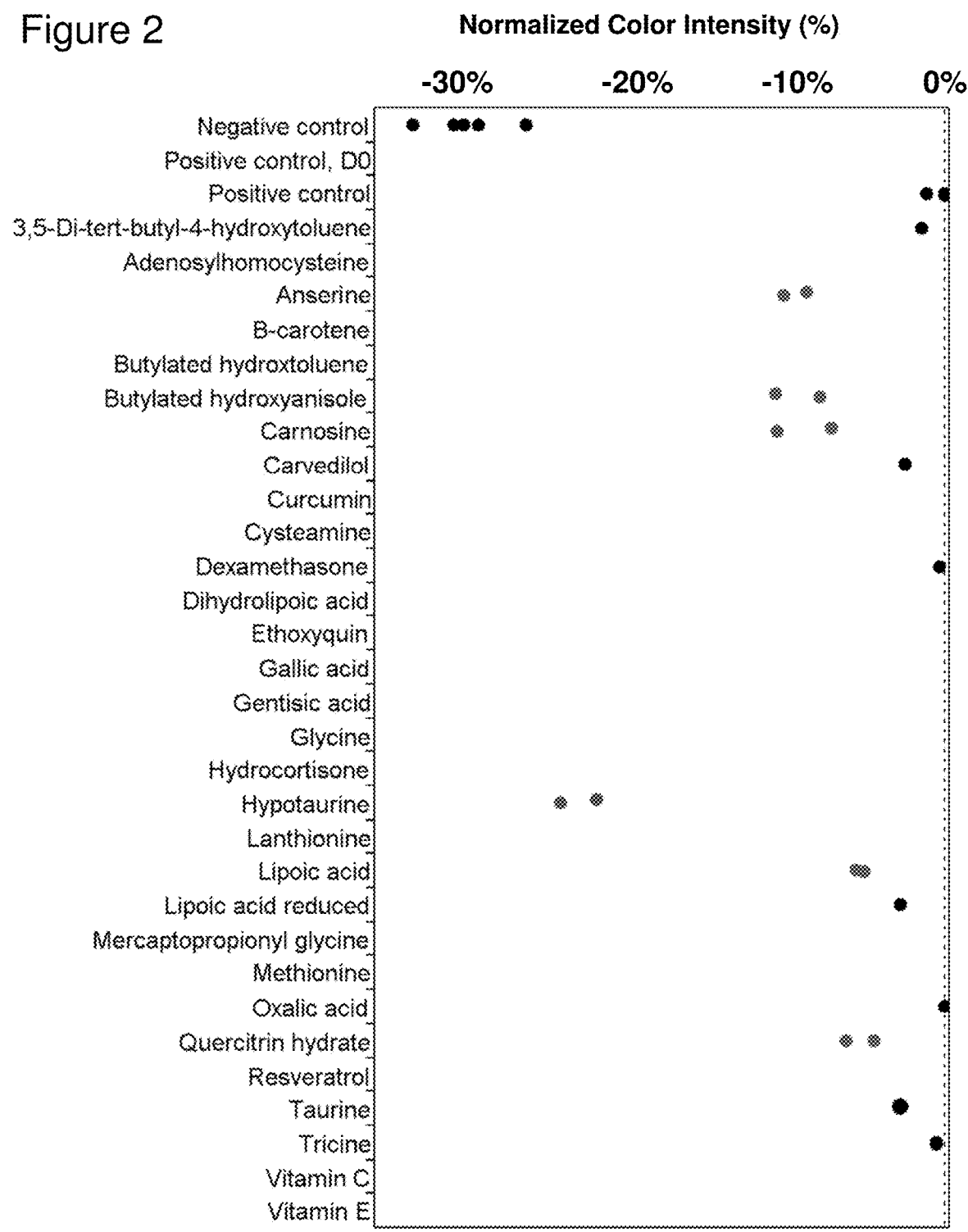
FIG. 2 is a subplot of FIG. 1 showing compounds that reduced color intensity in a representative cell culture medium containing an antibody. Numerical results were normalized to the positive control where the value for the positive control was set at 0% change in color intensity. Values lower than 0% indicate reduced color intensity.

After incubation, the monoclonal antibody was purified using protein A affinity chromatography. The pool was concentrated to 150 g/L using Amicon Centricon centrifugal filter devices (Millipore Corporation, Billerica, Mass.). Color intensity of the concentrated antibody composition was measured in the concentrated protein A pool using an assay wherein higher numerical values indicate higher color intensity and lower numerical values indicate lower color intensity. The numerical results were normalized to the positive control, where the value for the positive control was set at 0% change in color intensity. Of the 30 antioxidant compounds tested several compounds, such as gentisic acid, cysteamine, hydrocortisone, and mercaptopropionyl glycine, were found to increase the color of the antibody composition (FIG. 1). In comparison, six of the compounds such as hypotaurine, anserine, butylated hydroxyanisole, carnosine, lipoic acid, and quercitrin hydrate, were found to reduce the color of the antibody composition (FIG. 2). Of the antioxidants that reduced color intensity, hypotaurine demonstrated the greatest effect by reducing the color intensity of the antibody-containing compositions by approximately 25%. Taurine, an analog of hypotaurine, also reduced color intensity by approximately 5%.

TABLE 5

Representative components in media compositions tested

| Media Components | Media 1 (Basal) | Media 2 (Feed) | Media 3 (Basal) | Media 4 (Feed) |
|---|---|---|---|---|
| Iron (µM) | 75[a] | 0 | 18[b] | 0 |
| Vitamin B2 (mg/L) | 1.41 | 10 | 0.25 | 0 |
| Vitamin B6/Pyridoxine (mg/L) | 15.42 | 7 | 5.35 | 0 |
| Vitamin B6/Pyridoxal (mg/L) | 0 | 60 | 0 | 0 |
| Vitamin B9 (mg/L) | 9.93 | 197 | 8.61 | 0 |
| Vitamin B12 (mg/L) | 3.05 | 48 | 1.76 | 0 |
| Cysteine (mg/L) | 525 | 1500 | 0 | 1500 |
| Cystine (mg/L) | 0 | 0 | 480 | 0 |
| Hydrocortisone (nM) | 150 | 0 | 150 | 0 |

[a] Iron source is ferrous sulfate
[b] Iron source is ferric citrate

Figure 3:
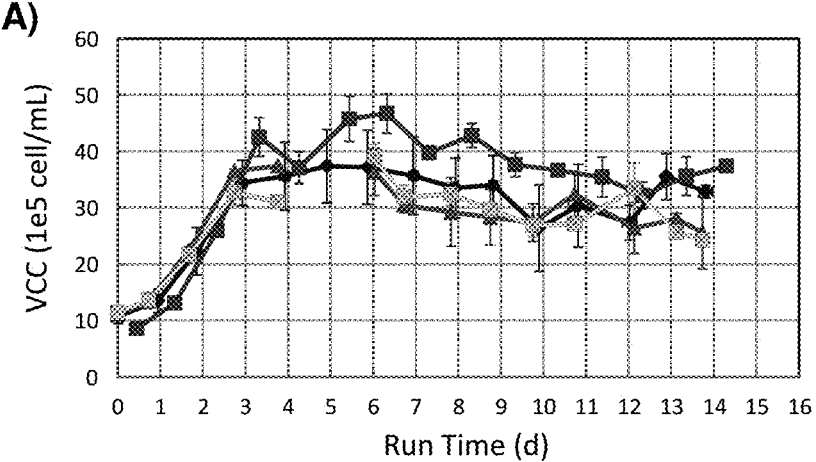
FIG. 3 is a series of graphs showing that a shaker flask cell culture model is comparable to the corresponding larger scale 2 L cell culture model. A) Cell growth in culture over the duration of incubation as measured by viable cell density (VCC) and expressed as number of cells per cell culture volume. B) Cell viability in cell culture over the duration of incubation as measured by the number of viable cells as a percentage of the total number of cells. C) Antibody production in cell culture over the duration of incubation as measured by high performance liquid chromatography and expressed as antibody titer. SF indicates shaker flask cell culture model. 2 L indicates a larger scale cell culture model.
Figure 3:
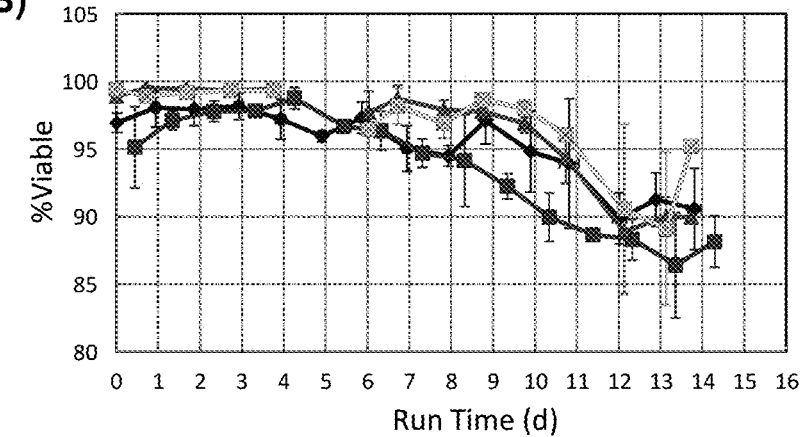
Figure 3:
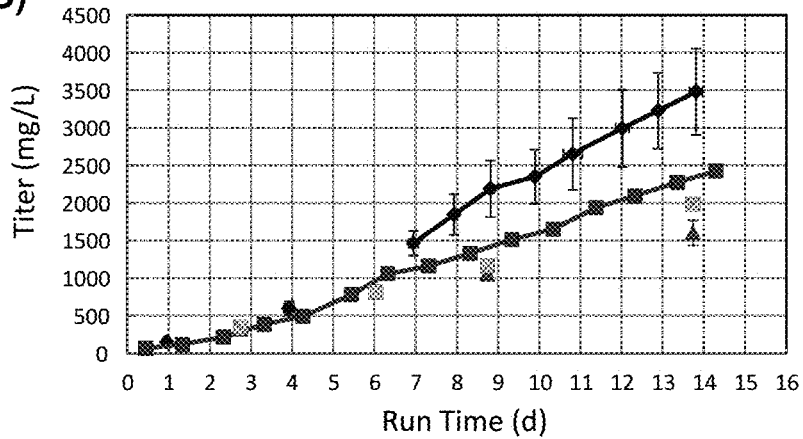

Example 2: Characterization of Antioxidant Compounds Capable of Reducing Color Intensity in Antibody Compositions Isolated from Antibody-Producing Cell Lines The ability of hypotaurine to reduce color intensity in antibody containing compositions obtained directly from cell cultures was evaluated. For these studies a shaker flask cell culture model was utilized that was found to be representative of larger scale 2 L cell culture. Briefly, for the shaker flask cell culture model, antibody producing CHO cells were inoculated at approximately $1.0 \times 10^6$ cells/mL in a 250 mL flask containing 100 mL of basal Media 1 or basal Media 3. For the larger scale 2 L cell cultures, antibody producing CHO cells were inoculated at approximately $1.0 \times 10^6$ cells/mL in 2-liter stirred bioreactors (Applikon, Foster City, Calif.) containing 1 L of basal Media 1 or basal Media 3. For the larger scale cell growth model, cells were cultured in fed-batch mode with addition of 100 mL of feed Media 2 if cultured in basal Media 1, or with 100 mL of feed Media 4 if cultured in basal Media 3, per liter of cell culture fluid at days 3, 6 and 9 for initiation of the production phase. For the shaker flask cell culture model, the cells were cultured in fed-batch mode with addition of 10 mL of feed Media 2 if cultured in basal Media 1, or with 10 mL mL of feed Media 4 if cultured in basal Media 3, per liter of cell culture fluid at days 3, 6 and 9 for initiation of the production phase. The concentration of glucose was analyzed every day and if the glucose concentration fell below 3 g/L, it was replenished from a 500 g/L stock solution of glucose for prevention of glucose depletion. Reactors were equipped with calibrated dissolved oxygen, pH and temperature probes. Dissolved oxygen was controlled on-line through sparging with air and/or oxygen. For the larger scale 2 L cell culture, pH was controlled through addition of $CO_2$ or $Na_2CO_3$ and antifoam was added to the cultures as needed. The cell cultures were maintained at pH 7.0 and a temperature of 37° C. from days 0 through 3, and then at 35° C. after day 3. The cell cultures were agitated at 275 rpm and the dissolved oxygen level was at 30% of air saturation. For the shaker flask cell cultures, cultures were placed on a shaker platform and agitated at 150 rpm in a 5% $CO_2$ incubator with a temperature of 37° C. from day 0 up to day 3 of the cell culture cycle with a temperature shift to 35° C. on day 4 until the end of the cell culture cycle at day 14. Osmolality was monitored using an osmometer from Advanced Instruments (Norwood, Mass.). Offline pH and metabolite concentrations were also determined daily using a Nova Bioprofile 400 (Nova Biomedical, Waltham, Mass.). Viable cell density (VCC) and cell viability was measured daily using a ViCell® automated cell counter (Beckman Coulter, Fullerton, Calif.). The cell culture fluid was collected daily by centrifuging 1 mL of cell culture fluid for determination of antibody titer using high performance liquid chromatography. At the end of the cell culture duration on day 14, the cell culture fluid from all samples was harvested by centrifugation. The monoclonal antibody in the harvested cell culture fluid was purified using protein A affinity chromatography. The protein A pool was concentrated to 150 g/L using Amicon Centricon centrifugal filter devices (Millipore Corporation, Billerica, Mass.). Color intensity of the concentrated antibody composition was measured in the concentrated protein A pool using an assay wherein higher numerical values indicate higher color intensity and lower numerical values indicate lower color intensity. Growth as measured by VCC (FIG. 3A) and cell viability (FIG. 3B) were comparable between the larger scale (2 L) and shaker flask (SF) cell culture models regardless of the media used. Antibody production was slightly lower in the shaker flask cell culture model with the highest antibody production observed in the larger scale cell culture model incubated in Media 1 and Media 2 (FIG. 3C). Color intensity of antibody compositions obtained from the shaker flask cell culture model was lower at a value of 1.07 when cultured in Media 3 and Media 4 as compared to antibody compositions obtained from shaker flask cell culture compositions when cultured in Media 1 and Media 2 which had a value of 2.25. These experiments established that the shaker flask model was comparable to the 2 L cell culture model and was suitable for use in subsequent experiments.

Figure 4:
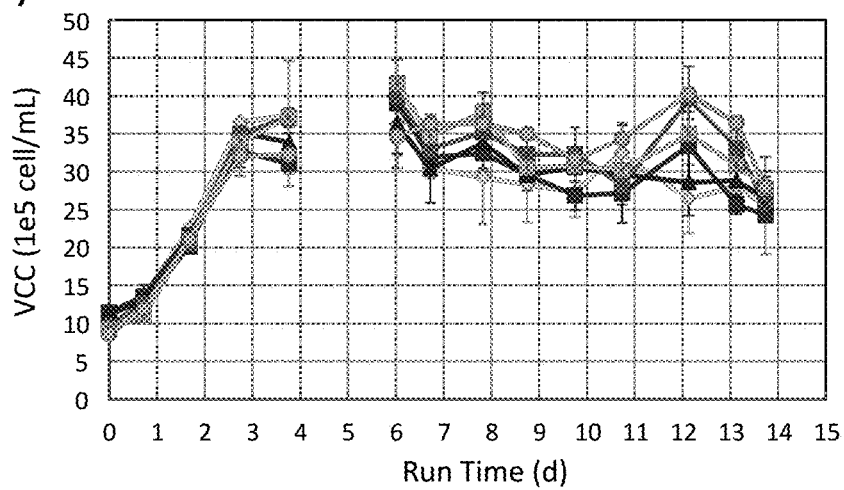
FIG. 4 is a series of graphs showing that addition of hypotaurine to cell culture media did not compromise cell growth, cell viability, or antibody production. A) Cell growth in culture over the duration of incubation as measured by VCC and expressed as number of cells per cell culture volume. B) Cell viability in cell culture over the duration of incubation as measured by the number of viable cells as a percentage of the total number of cells. C) Antibody production in cell culture over the duration of incubation as measured by high performance liquid chromatography and expressed as antibody titer.
Figure 4:
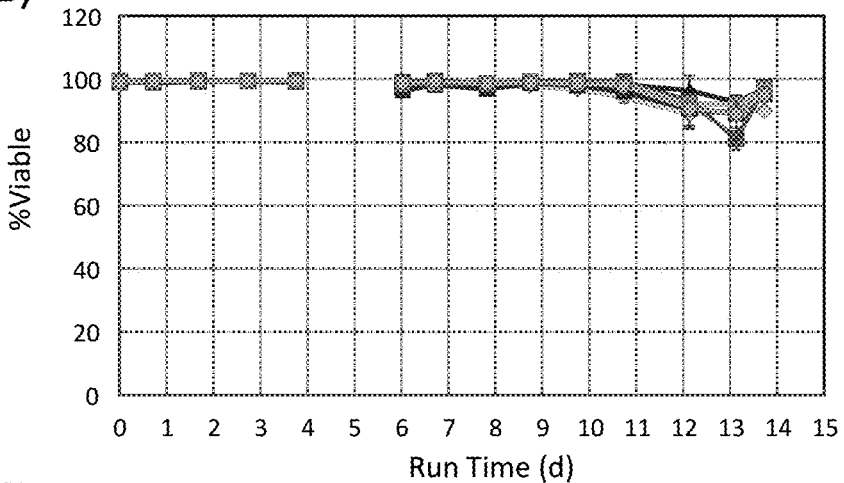
Figure 4:
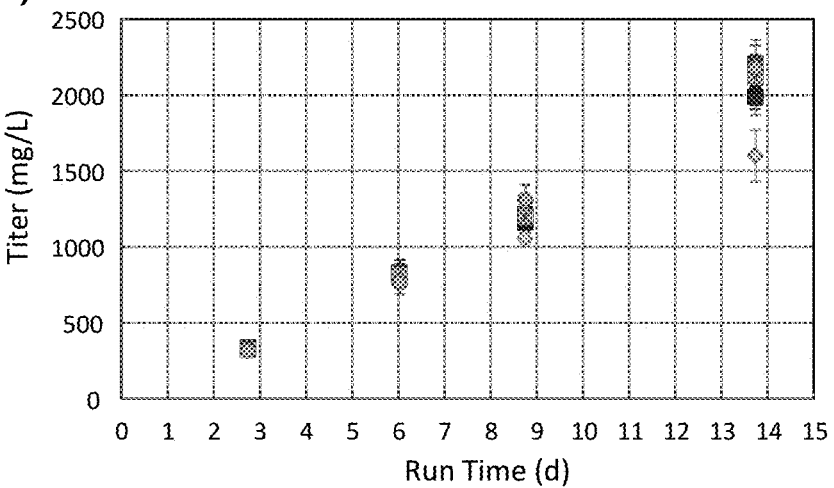
Figure 5:
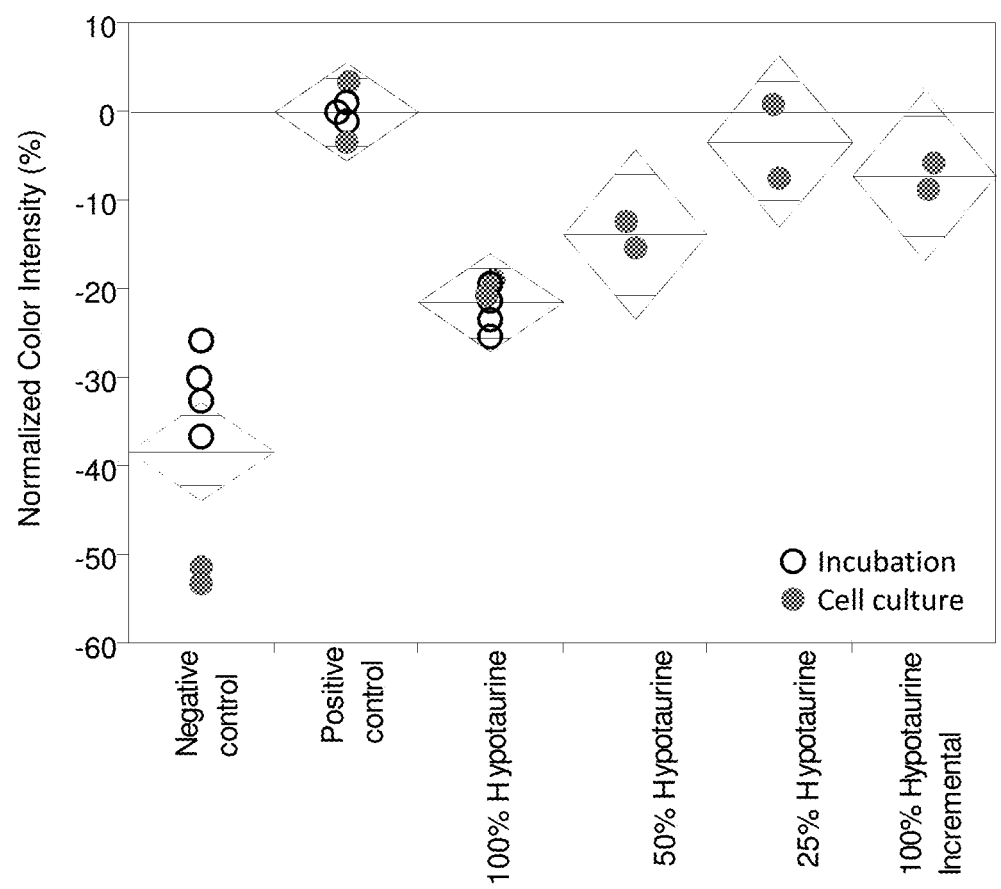
FIG. 5 is a graph showing color intensity of antibody compositions isolated from cell cultures grown in media supplemented with hypotaurine. 100%, 50%, or 25% indicates basal Media 1 supplemented with 9.16 mM, 4.58 mM or 2.29 mM hypotaurine, respectively. Filled circles indicate color intensity values for cell culture experiments. Empty circles indicate color intensity values for incubation screening experiments. Numerical results were normalized to the positive control, where the value for the positive control was set at 0% change in color intensity. Values lower than 0% indicate reduced color intensity.

For experimentation with cell culture media compositions that were supplemented with the antioxidant hypotaurine, antibody producing CHO cells were inoculated at approximately $1.0 \times 10^6$ cells/mL in a 250 mL flask containing 100 mL of basal Media 1. Media 1 was supplemented with 9.16 mM (100%), 4.58 mM (50%), or 2.29 mM (25%) hypotaurine for use in cell culture on Day 0. The cells were cultured in fed-batch mode with addition of 10 mL of feed Media 2 per liter of cell culture fluid at Days 3, 6 and 9 for initiation of the production phase. An additional experimental sample involved the incremental addition of 9.16 mM hypotaurine over the cell culture period. Specifically, 2.29 mM (25%)

hypotaurine was added on Day 0 of cell culture in basal Media 1, and 25% was added on Day 3, Day 6 and Day 9 in feed Media 2. A positive control was included by culturing cells in Media 1 and 2 without hypotaurine supplementation. The negative control was included by culturing cells cultured in Media 3 and Media 4 without hypotaurine supplementation. As described above, the concentration of glucose was analyzed every day and if the glucose concentration fell below 3 g/L, it was replenished from a 500 g/L stock solution of glucose for prevention of glucose depletion. The cell cultures were maintained at pH 7.0 and a temperature of 37° C. from days 0 through 3, and then at 35° C. after day 3. The cell cultures were agitated at 275 rpm and the dissolved oxygen level was at 30% of air saturation. VCC and cell viability was measured daily using a ViCell® automated cell counter (Beckman Coulter, Fullerton, Calif.). The cell culture fluid was collected daily by centrifuging 1 mL of cell culture fluid for determination of antibody titer using high performance liquid chromatography. At the end of the cell culture duration on day 14, the cell culture fluid from all samples was harvested by centrifugation. The monoclonal antibody in the harvested cell culture fluid was purified using protein A affinity chromatography. The protein A pool was concentrated to 150 g/L using Amicon Centricon centrifugal filter devices (Millipore Corporation, Billerica, Mass.). Color intensity of the concentrated antibody composition was measured in the concentrated protein A pool using an assay wherein higher numerical values indicate higher color intensity and lower numerical values indicate lower color intensity. The numerical results were normalized to the positive control, where the value for the positive control was set at 0% change in color intensity. Growth as measured by VCC (FIG. 4A) and cell viability (FIG. 4B) was comparable among all the cell cultures tested. Furthermore, with the exception of incremental addition of hypotaurine, cell cultures cultured in media supplemented with hypotaurine produced the same level of antibody titers as cell cultures cultured in media not containing hypotaurine (FIG. 4C). Color intensity was found to be reduced with higher concentration of hypotaurine with the greatest reduction observed in media containing 9.16 mM hypotaurine (FIG. 5). This reduction in color intensity was optimal when hypotaurine was added as a bolus at Day 1 rather than added incrementally over the course of cell culture incubation. Comparison of color intensity values obtained from cell culture experiments and incubation experiments (See Example 1) demonstrated that the results of the incubation screening experiments (FIG. 5, empty circles) correlated well with the results from cell culture experiments (FIG. 5, filled circles).

Figure 6:
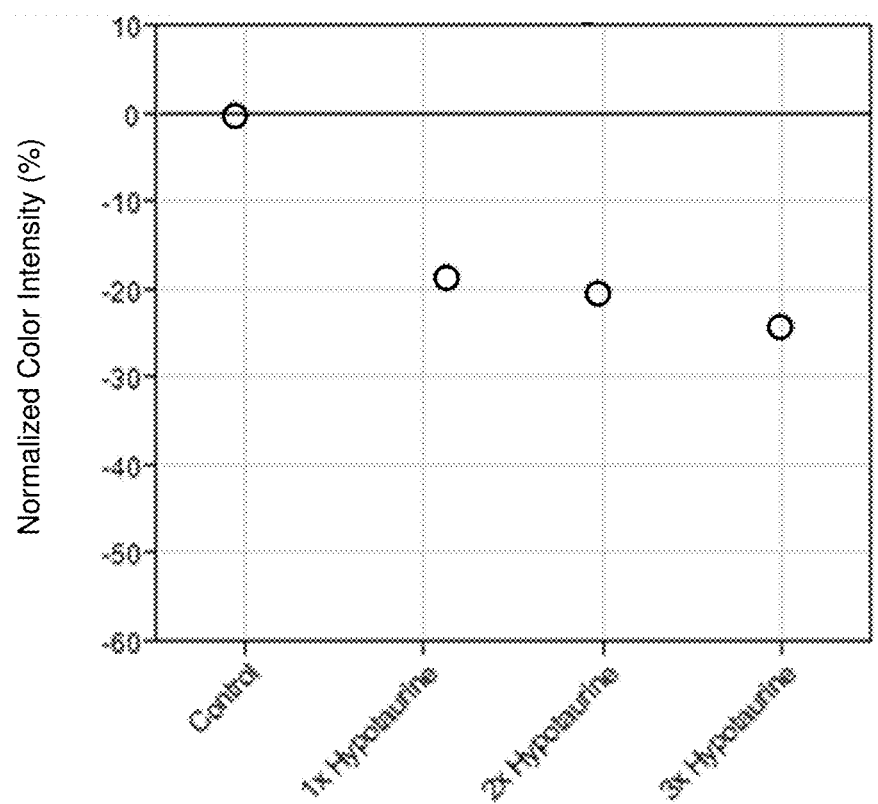
FIG. 6 is a graph showing color intensity of antibody compositions isolated from cell cultures grown in media supplemented with hypotaurine. 3×, 2×, or 1× indicates basal Media 3 supplemented with 38.85 mM, 25.9 mM or 12.95 mM hypotaurine, respectively. Filled circles indicate color intensity values for cell culture experiments. Numerical results were normalized to the positive control, where the value for the positive control was set at 0% change in color intensity. Values lower than 0% indicate reduced color intensity.

Similar experiments were conducted for antibody compositions isolated from cell cultures harvested in basal Media 3 and feed Media 4 to determine if the color reducing effect of hypotaurine extended to other cell culture media. Briefly, as above, antibody producing CHO cells were inoculated at approximately $1.0 \times 10^6$ cells/mL in a 250 mL flask containing 100 mL of basal Media 3. Media 3 was supplemented with 12.95 mM (1×), 25.9 mM (2×), or 38.85 mM (3×) hypotaurine for use in cell culture on Day 0. The cells were cultured in fed-batch mode with addition of 10 mL of feed Media 4 per liter of cell culture fluid at Days 3, 6 and 9 for initiation of the production phase. A positive control was included by culturing cells in Media 1 and 2 without hypotaurine supplementation. The cultures were placed on a shaker platform and agitated at 150 rpm in a 5% $CO_2$ incubator with a temperature of 37° C. from day 0 up to day 3 of the cell culture cycle with a temperature shift to 35° C. on day 4 until the end of the cell culture cycle at day 14. Osmolality, offline pH and metabolite concentrations were measured as described above. VCC and cell viability was measured daily using a ViCell® automated cell counter (Beckman Coulter, Fullerton, Calif.). The cell culture fluid was collected daily by centrifuging 1 mL of cell culture fluid for determination of antibody titer using high performance liquid chromatography. At the end of the cell culture duration on day 14, the cell culture fluid from all samples was harvested by centrifugation. The monoclonal antibody in the harvested cell culture fluid was purified using protein A affinity chromatography. The protein A pool was concentrated to 150 g/L using Amicon Centricon centrifugal filter devices (Millipore Corporation, Billerica, Mass.). Color intensity of the concentrated antibody composition was measured in the concentrated protein A pool using an assay wherein higher numerical values indicate higher color intensity and lower numerical values indicate lower color intensity. The numerical results were normalized to the positive control, where the value for the positive control was set at 0% change in color intensity. Color intensity was found to be reduced with higher concentration of hypotaurine with the greatest reduction observed in media containing 38.85 mM hypotaurine (FIG. 6).

Figure 7:
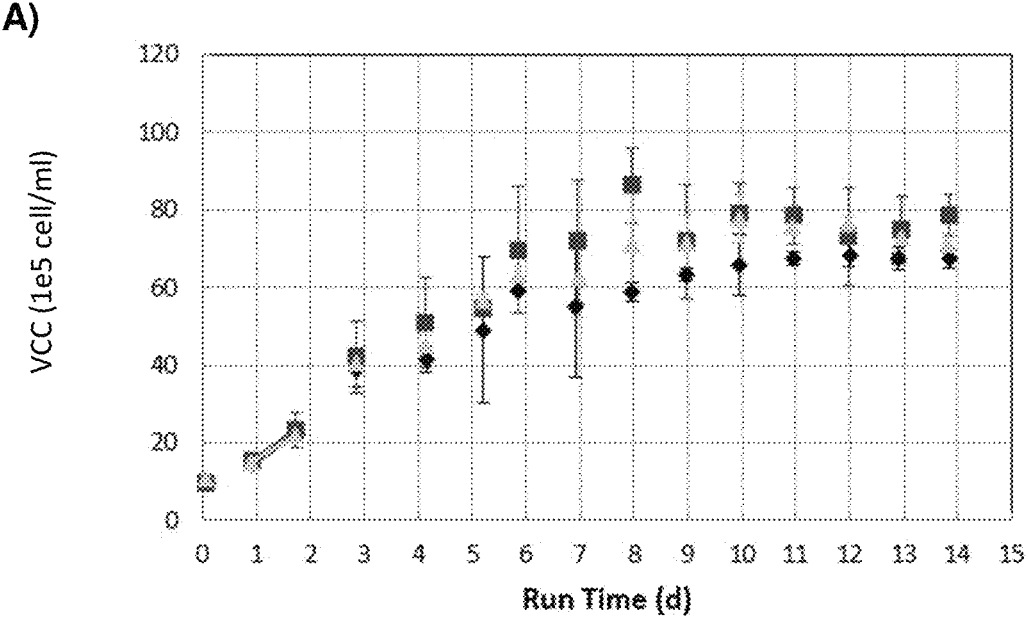
FIG. 7 contains graphs showing that addition of hypotaurine, or carboxy methyl cysteine to media did not compromise cell growth or cell viability. A) Cell growth in culture over the duration of incubation as measured by VCC and expressed as number of cells per cell culture volume. B) Cell viability in culture over duration of incubation expressed as percent of total culture volume.
Figure 7:
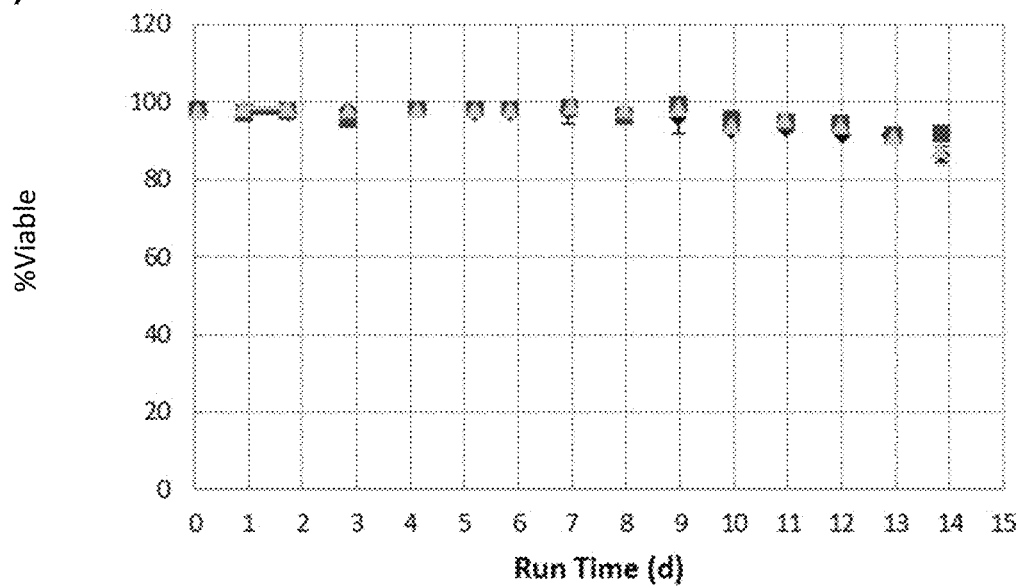
Figure 7:
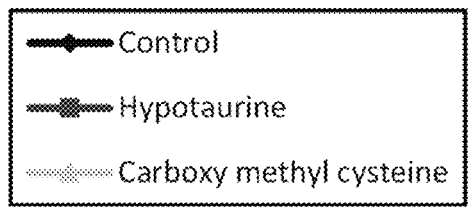
Figure 8:
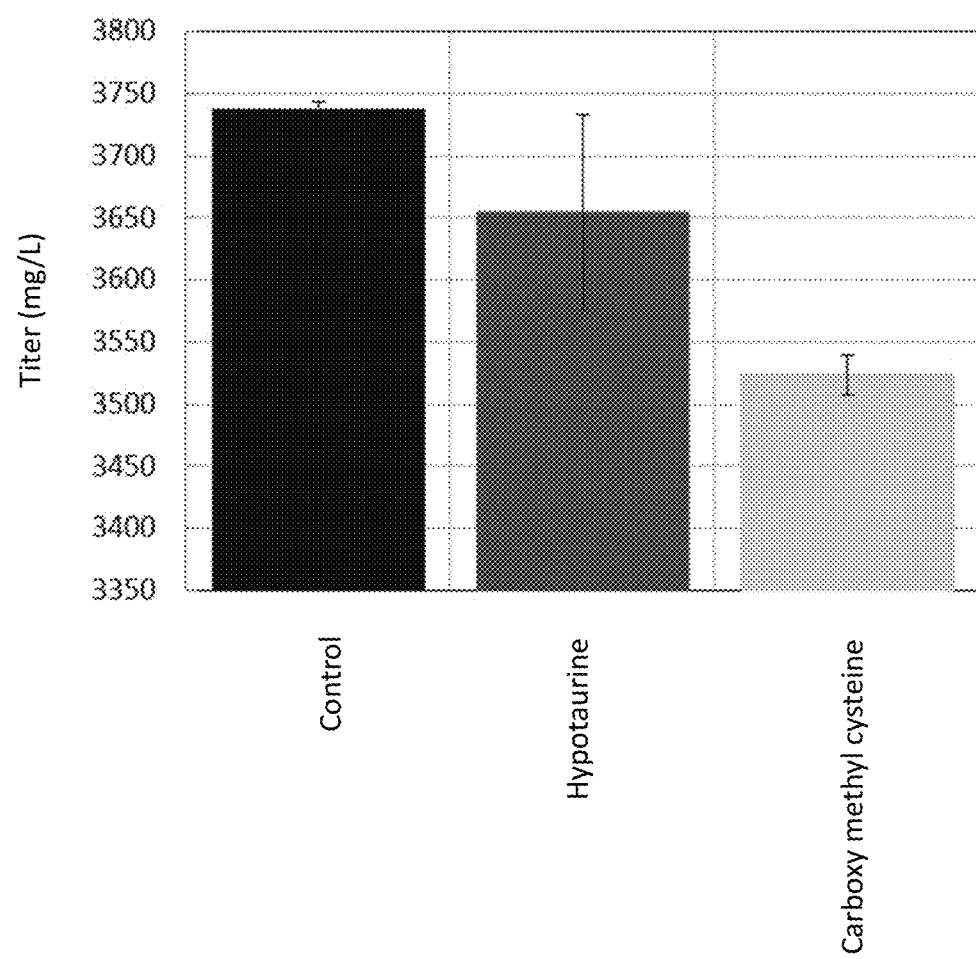
FIG. 8 is a graph showing that addition of hypotaurine, or carboxy methyl cysteine to media did not significantly reduce antibody production. Antibody production in cell culture over the duration of incubation was measured by high performance liquid chromatography and expressed as antibody titer.
Figure 9:
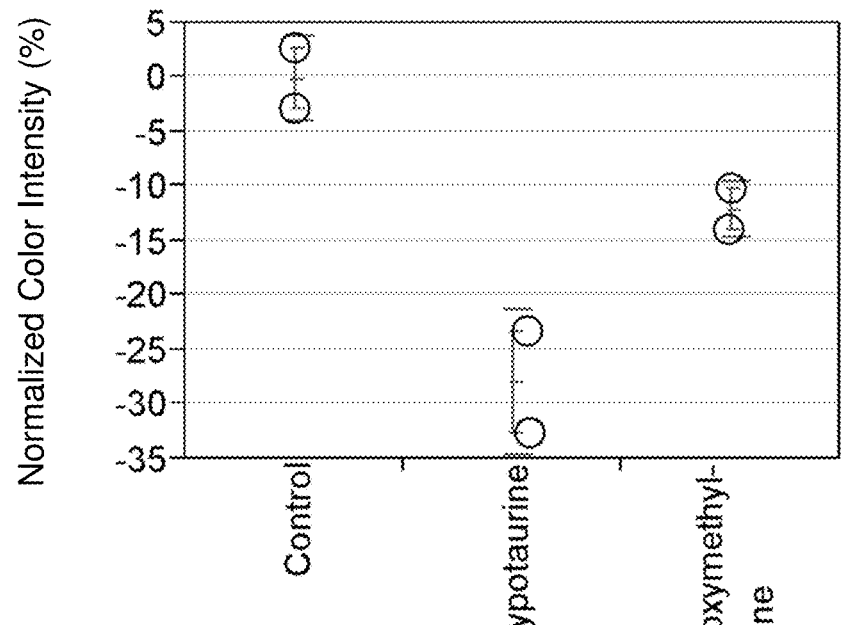
FIG. 9 is a graph showing color intensity of antibody compositions isolated from cell cultures grown in media supplemented with hypotaurine or carboxy methyl cysteine. A and B) Indicate two different color assays used to measure color intensity. Numerical results were normalized to the positive control where the value for the positive control was set at 0% change in color intensity. Values lower than 0% indicate reduced color intensity.
Figure 9:
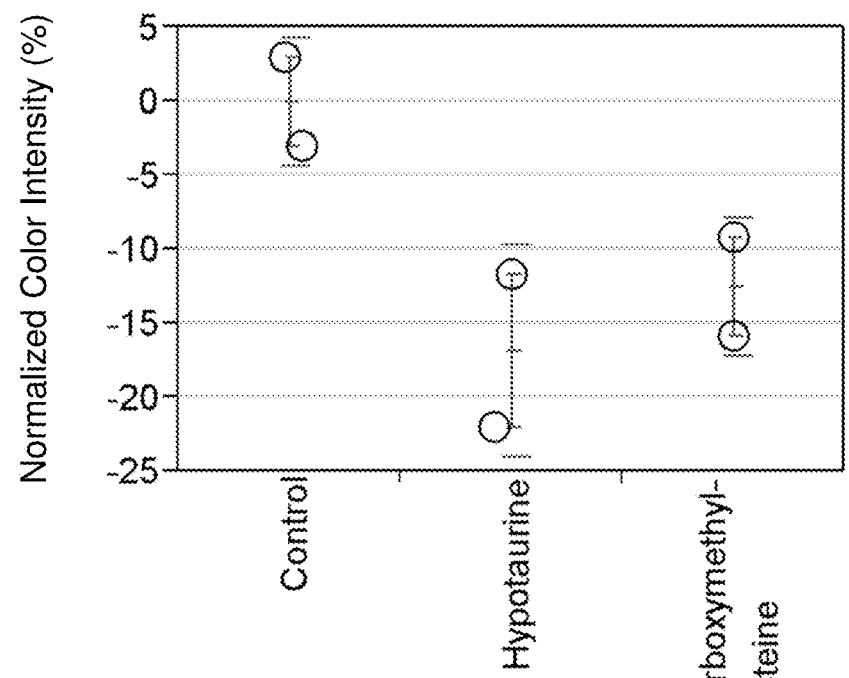

Example 3: Characterization of Hypotaurine Analogs in Reduction of Color in Antibody Compositions Isolated from Antibody-Producing Cell Lines Hypotaurine analogs were tested to assess if they demonstrated a color reducing effect in antibody containing compositions. Antibody producing CHO cells were inoculated at approximately $1.0 \times 10^6$ cells/mL in 2-liter stirred bioreactors (Applikon, Foster City, Calif.) containing 1 L of basal Media 1 supplemented with 12.95 mM hypotaurine or 10 mM carboxymethylcysteine (CAS number 638-23-3). Cells were cultured in fed-batch mode with addition of 100 mL of feed Media 2 per liter of cell culture fluid at days 3, 6 and 9 for initiation of the production phase. A positive control was included by culturing cells in Media 1 and 2 without hypotaurine supplementation. The concentration of glucose was analyzed every day and if the glucose concentration fell below 2 g/L, it was replenished from a 1.5 g/L stock solution of glucose for prevention of glucose depletion. Reactors were equipped with calibrated dissolved oxygen, pH and temperature probes. Dissolved oxygen was controlled on-line through sparging with air and/or oxygen. pH was controlled through addition of $CO_2$ or $Na_2CO_3$ and antifoam was added to the cultures as needed. The cell cultures were maintained at pH 7.0 and a temperature of 37° C. from days 0 through 3, and then at 35° C. after day 3. The cell cultures were agitated at 275 rpm and the dissolved oxygen level was at 30% of air saturation. Osmolality was monitored using an osmometer from Advanced Instruments (Norwood, Mass.). Offline pH and metabolite concentrations were also determined daily using a Nova Bioprofile 400 (Nova Biomedical, Waltham, Mass.). VCC and cell viability was measured daily using a ViCell® automated cell counter (Beckman Coulter, Fullerton, Calif.). The cell culture fluid was collected daily by centrifuging 1 mL of cell culture fluid for determination of antibody titer using high performance liquid chromatography. At the end of the cell culture duration on day 14, when the amount of protein in the culture was approximately 2-10 g/L, the cell culture fluid from all samples was harvested by centrifugation. The monoclonal antibody in the harvested cell culture fluid was purified using protein A affinity chromatography. The protein A pool was concentrated to 150 g/L using Amicon Centricon centrifugal filter devices (Millipore Corporation, Billerica, Mass.). Color intensity of the concentrated antibody composition was measured in the concentrated protein A pool using two different assays wherein higher numerical values indicated higher color intensity and lower numerical values indicated lower color intensity. Growth as measured by VCC (FIG. 7A) and cell viability (FIG. 7B) was comparable among all cell cultures tested. Cell cultures cultured in media supplemented with hypotaurine or carboxymethylcysteine produced comparable levels of antibody titers (FIG. 8). Using a specific color assay, color intensity of isolated antibody composition was found to be reduced by 27% and 13% when antibody-producing cells were cultured media supplemented with hypotaurine and carboxymethylcysteine, respectively (FIG. 9A). This color intensity reduction was confirmed by using a second color assay which detected an approximate 17% and 13% color intensity reduction in antibody compositions isolated from cell cultured in media supplemented with hypotaurine and carboxymethylcysteine, respectively (FIG. 9B).

The invention claimed is:

1. A method of producing a recombinant polypeptide composition with reduced color intensity, comprising the steps of:
    culturing a Chinese hamster ovary (CHO) cell comprising a nucleic acid encoding the recombinant polypeptide in a cell culture medium, wherein the cell culture medium comprises one or more of components (a)-(h):
        (a) hypotaurine,
        (b) s-carboxymethylcysteine,
        (c) carnosine,
        (d) anserine,
        (e) butylated hydroxyanisole,
        (f) lipoic acid,
        (g) quercitrin hydrate, and
        (h) taurine; and
    producing the recombinant polypeptide;
wherein the cell culture medium comprising the one or more of components (a)-(h) reduces the color intensity of the composition comprising the recombinant polypeptide produced by the cell as compared to a composition comprising the recombinant polypeptide produced by the cell cultured in a cell culture medium that does not comprise the one or more of components (a)-(h).

2. The method of claim 1, wherein the cell culture medium comprising the one or more of components (a)-(h) reduces the color intensity of the composition comprising the recombinant polypeptide produced by the cells by at least about 0.1% as compared to the composition comprising the recombinant polypeptide produced by the cell cultured in a cell culture medium that does not comprise the one or more of components (a)-(h).

3. The method of claim 1, wherein the cell culture medium comprising the one or more of components (a)-(h) reduces the color intensity of the composition comprising the recombinant polypeptide produced by the cells by about 5% to about 50% as compared to the composition comprising the recombinant polypeptide produced by the cell cultured in a cell culture medium that does not comprise the one or more of components (a)-(h).

4. The method of claim 1, wherein the cell culture medium comprises the one or more components (a)-(h) in an amount selected from the group consisting of:
    (a) hypotaurine at a concentration from at least about 0.0001 mM;
    (b) s-carboxymethylcysteine at a concentration from at least about 0.0001 mM;
    (c) carnosine at a concentration from at least about 0.0001 mM;
    (d) anserine at a concentration from at least about 0.0001 mM;
    (e) butylated hydroxyanisole at a concentration from at least about 0.0001 mM;
    (f) lipoic acid at a concentration from at least about 0.0001 mM;
    (g) quercitrin hydrate at a concentration from at least about 0.0001 mM; and
    (h) taurine at a concentration from at least about 0.0001 mM.

5. The method of claim 4, wherein the cell culture medium comprises hypotaurine at a concentration from about 2.0 mM to about 50.0 mM.

6. The method of claim 4, wherein the cell culture medium comprises s-carboxymethylcysteine at a concentration from about 8.0 mM to about 12.0 mM.

7. The method of claim 4, wherein the cell culture medium comprises carnosine at a concentration from about 8.0 mM to about 12.0 mM.

8. The method of claim 4, wherein the cell culture medium comprises anserine at a concentration from about 3.0 mM to about 5.0 mM.

9. The method of claim 4, wherein the cell culture medium comprises butylated hydroxyanisole at a concentration from about 0.025 mM to about 0.040 mM.

10. The method of claim 4, wherein the cell culture medium comprises lipoic acid at a concentration from about 0.040 mM to about 0.060 mM.

11. The method of claim 4, wherein the cell culture medium comprises quercitrin hydrate at a concentration from about 0.010 mM to about 0.020 mM.

12. The method of claim 1, wherein the cell culture medium is a chemically defined cell culture medium.

13. The method of claim 1, wherein the cell culture medium is a chemically undefined cell culture medium.

14. The method of claim 1, wherein the cell culture medium is a basal cell culture medium.

15. The method of claim 1, wherein the cell culture medium is a feed cell culture medium.

16. The method of claim 1, wherein the cell is contacted with the cell culture medium during the cell's growth phase.

17. The method of claim 1, wherein the cell is contacted with the cell culture medium during the cell's production phase.

18. The method of claim 1, wherein the one or more of components (a)-(h) is added to the cell culture medium on at least one day of a cell culture cycle.

19. The method of claim 1, wherein the one or more of components (a)-(h) is added to the cell culture medium on day 0 of a 14 day cell culture cycle.

20. The method of claim 1, further comprising the step of recovering the recombinant polypeptide from the cell culture medium comprising one or more of components (a)-(h).

21. The method of claim 20, wherein a composition comprising the recovered recombinant polypeptide is a liquid composition or a non-liquid composition.

22. The method of claim 21, wherein the composition comprising the recovered recombinant polypeptide appears as a colorless or slightly colored liquid.

23. The method of claim 1, comprising purifying the recombinant polypeptide.

24. The method of claim 23, wherein the cell culture medium comprises the hypotaurine, and wherein the cell culture medium comprising the hypotaurine reduces the color intensity of the composition comprising the recombinant polypeptide produced by the cell as compared to a composition comprising the recombinant polypeptide produced by the cell cultured in a cell culture medium that does not comprise the hypotaurine.

25. The method of claim 23, wherein the cell culture medium comprises the s-carboxymethylcysteine, and wherein the cell culture medium comprising the s-carboxymethylcysteine reduces the color intensity of the composition comprising the recombinant polypeptide produced by the cell as compared to a composition comprising the recombinant polypeptide produced by the cell cultured in a cell culture medium that does not comprise the s-carboxymethylcysteine.

26. The method of claim 23, wherein the cell culture medium comprises the carnosine, and wherein the cell culture medium comprising the carnosine reduces the color intensity of the composition comprising the recombinant polypeptide produced by the cell as compared to a composition comprising the recombinant polypeptide produced by the cell cultured in a cell culture medium that does not comprise the carnosine.

27. The method of claim 23, wherein the cell culture medium comprises the anserine, and wherein the cell culture medium comprising the anserine reduces the color intensity of the composition comprising the recombinant polypeptide produced by the cell as compared to a composition comprising the recombinant polypeptide produced by the cell cultured in a cell culture medium that does not comprise the anserine.

28. The method of claim 23, wherein the cell culture medium comprises the taurine, and wherein the cell culture medium comprising the taurine reduces the color intensity of the composition comprising the recombinant polypeptide produced by the cell as compared to a composition comprising the recombinant polypeptide produced by the cell cultured in a cell culture medium that does not comprise the taurine.

29. The method of claim 23, wherein the cell culture medium comprises the lipoic acid, and wherein the cell culture medium comprising the lipoic acid reduces the color intensity of the composition comprising the recombinant polypeptide produced by the cell as compared to a composition comprising the recombinant polypeptide produced by the cell cultured in a cell culture medium that does not comprise the lipoic acid.

30. The method of claim 23, wherein the cell culture medium comprises the quercitrin hydrate, and wherein the cell culture medium comprising the quercitrin hydrate reduces the color intensity of the composition comprising the recombinant polypeptide produced by the cell as compared to a composition comprising the recombinant polypeptide produced by the cell cultured in a cell culture medium that does not comprise the quercitrin hydrate.

31. The method of claim 4, wherein the cell culture medium comprises taurine at a concentration from about 1.0 mM to about 10 mM.

32. The method of claim 23, wherein the cell culture medium comprises the quercitrin hydrate, and wherein the cell culture medium comprising the quercitrin hydrate reduces the color intensity of the composition comprising the recombinant polypeptide produced by the cell as compared to a composition comprising the recombinant polypeptide produced by the cell cultured in a cell culture medium that does not comprise the quercitrin hydrate.

* * * * *